United States Patent [19]

Rieke

[11] Patent Number: 5,384,078
[45] Date of Patent: Jan. 24, 1995

[54] SOLUBLE HIGHLY REACTIVE FORM OF CALCIUM AND REAGENTS THEREOF

[75] Inventor: Reuben D. Rieke, Lincoln, Nebr.

[73] Assignee: Board of Regents of the University of Nebraska, Lincoln, Nebr.

[21] Appl. No.: 167,726

[22] Filed: Dec. 15, 1993

Related U.S. Application Data

[63] Continuation of Ser. No. 62,135, May 17, 1993, abandoned, which is a continuation-in-part of Ser. No. 738,828, Aug. 1, 1991, Pat. No. 5,211,889.

[51] Int. Cl.$^6$ .................... C07F 3/04; C07D 305/00; C07D 309/00; C07C 2/02
[52] U.S. Cl. .................... 260/665 R; 549/263; 549/264; 549/265; 549/273; 549/275; 546/16; 585/502; 585/520
[58] Field of Search ............ 260/665 R; 549/263, 549/264, 265, 273, 275; 546/16, 23, 24; 585/502, 520

[56] References Cited

U.S. PATENT DOCUMENTS

| | | | |
|---|---|---|---|
| 4,069,267 | 1/1978 | Kamienski et al. | 260/665 R |
| 4,087,468 | 5/1978 | Solomon | 568/807 |
| 4,166,898 | 9/1979 | Kambe | 528/405 |
| 4,325,840 | 4/1982 | Malpass | 252/431 R |
| 4,396,554 | 8/1983 | Robinson et al. | 260/665 R |
| 4,731,203 | 3/1988 | Bogdanovic | 260/665 G |
| 5,211,886 | 5/1993 | Rieke | 260/665 R |
| 5,231,205 | 7/1993 | Rieke | 260/66 R X |

FOREIGN PATENT DOCUMENTS 2027257 4/1991 Canada.

OTHER PUBLICATIONS

S. Akutagawa et al., "Metal-Assisted Terpenoid Synthesis. 3. A Myrcene Magnesium Compound as a New Example of an Enediylmetal System Formed from a Conjugated Diene and Its Synthetic Applications," *J. Am. Chem. Soc.*, 98, 7420–7421 (1976).
A. Alexakis et al., "Organocopper Conjugate Addition Reaction in the Presence of Trimethylchlorosilane," *Tetrahedron Lett.*, 27, 1047–1050 (1986).
R. T. Arnold et al., "Activated Metals. A Procedure for the Preparation of Activated Magnesium and Zinc", *Synthetic Communications*, 7, 223–232 (1977).
R. Baker et al., "Reaction of 'Myrcene-Magnesium' with Esters, Acetyl Chloride, and Acetic Anhydride: Formation of Cyclopentenols and Cyclopropane Derivatives," *J. C. S. Perkin I*, 1815–1818 (1976).
S. C. Berk et al., "General Approach to Highly Functionalized Benzylic Organometallics of Zinc and Copper," *J. Org. Chem.*, 53, 5789–5791 (1988).

(List continued on next page.)

*Primary Examiner*—Arthur C. Prescott
*Attorney, Agent, or Firm*—Merchant, Gould, Smith, Edell, Welter & Schmidt

[57] ABSTRACT

A soluble highly reactive form of calcium, prepared from Ca(II) salts and a reducing agent in ethereal, polyethereal, or hydrocarbon solvents, is presented. This form of calcium can be used in the preparation of organocalcium reagents. The organocalcium reagents resulting from the reaction of the soluble highly reactive calcium with organic compounds containing either halide, cyanide, a 1,3-diene, or a polyunsaturated functionality, are stable, useful reagents for organic synthesis. The organocalcium halide reagents undergo Grignard-type reactions. They also undergo reactions with Cu(I) salts to form organocalcium cuprate reagents. The organocalcium cuprate reagents undergo a variety of cross-coupling reactions. The soluble highly reactive calcium reacts with 1,3-dienes to yield the corresponding 2-butene-1,4-diylcalcium complexes. These bis-organocalcium reagents can undergo dialkylation reactions with α,ω-alkylene dihalides and dichlorosilanes to form the corresponding 3-, 5-, and 6-membered ring derivatives. The soluble highly reactive calcium also reacts with organic dihalides to form mono- or diorganocalcium compounds which can be converted into a wide variety of polymers.

35 Claims, No Drawings

OTHER PUBLICATIONS

A. V. Bogat-skii et al., "Calcium–Containing Organic Compounds. II. Preparation of Organocalcium Compounds and Study of Their Properties," *Zhurnal Obschei Khimii*, 47, 2297–2305 (1977) (with English translation).

B. Bogdanovic, "Magnesium Anthracene Systems and Their Application in Synthesis and Catalysis," *Acc. Chem. Res.*, 21, 261–267 (1988).

T. P. Burns et al., "Preparation of Grignard Reagents from 3–Halo Ethers," *J. Org. Chem.*, 48, 4141–4143 (1983).

T. P. Burns et al., "Highly Reactive Magnesium and Its Application to Organic Syntheses," *J. Org. Chem.*, 52, 3674–3680 (1987).

T.—A. Chen et al., "The First Regioregular Head-to-Tail Poly(3–hexylthiophene–2,5–diyl) and a Regiorandom Isopolymer: Ni vs. Pd Catalysis of 2(5)–Bromo–5(-2)–(bromozincio)–3–hexylthiophene Polymerization," *J. Am. Chem. Soc.*, 114, 10087–10088 (1992).

E. J. Corey et al., "The Reactions of Combined Organo–cuprate–Chlorotrimethylsilane Reagents with Conjugated Carbonyl Compounds," *Tetrahedron Lett.*, 26, 6019–6022 (1985).

J. E. Dubois et al., "Magnesiens encombres a structure cage: synthese du bromure d'adamantyl-1 magnesium," *C. R. Acad. Sci. Ser.*, 284, 145–148 (1977).

U. M. Dzemilev et al., "Synthesis and Transformations of 'Non–Grignard' Organomagnesium Reagents Obtained from 1,3–Dienes," *J. Organomet. Chem.*, 406, 1–47 (1991).

G. W. Ebert et al., "Preparation of Aryl, Alkynyl, and Vinyl Organocopper Compounds by the Oxidative Addition of Zerovalent Copper to Carbon–Halogen Bonds," *J. Org. Chem.*, 53, 4482–4488 (1988).

E. Erdik, "Copper(I) Catalyzed Reactions of Organolithiums and Grignard Reagents," *Tetrahedron*, 40, 641–657 (1984).

G. Erker et al., "The Remarkable Features of ($\eta^4$–Conjugated Diene) zirconocene and —hafnocene Complexes," *Adv. Organomet. Chem.*, 24, 1–39 (1985).

L. F. Fieser et al., "Synthesis of Keto Acids by Chromic Anhydride Oxidation of Tertiary Alcohols," *J. Am. Chem. Soc.*, 70, 3352–3355 (1948).

P. K. Freeman et al., "Magnesium Anthracene Dianion," *J. Org. Chem.*, 48, 879–881 (1983).

K. Fujita et al., "Magnesium–Butadiene Addition Compounds: Isolation, Structural Analysis and Chemical Reactivity," *J. Organomet. Chem.*, 113, 201–213 (1976).

B. G. Gowenlock et al., "The Organometallic Chemistry of the Alkaline Earth Metals," *J. Organomet. Chem. Library, Organomet. Chem. Rev.*, 3, 1–73 (1977).

T. P. Hanusa, "New Developments in the Organometallic Chemistry of Calcium, Strontium and Barium," *Polyhedron*, 9, 1345–1362 (1990).

S. Harvey, et al., "Polymer Supported 'Magnesium(anthracene)': Effective in Forming Benzylic Grignard Reagents (via Electron Transfer Reactions)," *J.C.S. Chem. Commun.*, 652–653 (1988).

S. Harvey et al., "Main Group Conjugated Organic Anion Chemistry. 3. Application of Magnesium–Anthracene Compounds in the Synthesis of Grignard Reagents," *J. Org. Chem.*, 53, 3134–3140 (1988).

S. Itsuno et al., "The First Direct Formation of a Grignard Reagent on an Insoluble Polymer," *J. Org. Chem.*, 52, 4644–4645 (1987).

Y. Kai et al., "The X–Ray Structure of a Magnesium–1,3–Diene Complex, The Unique Mode of Coordination of Diene Observed in Penta–Coordinated MG(THF)$_3$(s–cis–PhCH=CH—CH=CHPh)," *Chem. Lett., 1277–1280 (1982)*.

N. Kawabata et al., "Preparation of Organocalcium Halides," *Tetrahedron*, 29, 1069–1071 (1973).

N. Kawabata et al., "Preparation of Organocalcium Halides in Hydrocarbon Solvents," *J. Org. Chem.*, 38, 4268–4270 (1973).

D. W. Knight, "Saturated Carbocyclic Ring Synthesis," *Gen. Synth. Methods*, 6, 277–(1983).

H. Kroto, "C$_{60}$ fullerenes, giant fullerenes and soot," *Pure & Appl. Chem.*, 62, 407–415 (1990).

W. E. Lindsell, "Magnesium, Calcium, Strontium and Barium," *Comprehensive Organometallic Chemistry*, Ch. 4.1 and 4.2; Wilkinson, Stone & Abel, ed.; Pergamon Press, Oxford (1982); pp. 155–252.

B. H. Lipshutz et al., "Reactions of Stoichiometric Higher Order, Mixed Lithio Magnesio Organocuprates," *Tetrahedron*, 42, 2873–2879 (1986).

R. M. Magid, "Nucleophilic and Organometallic Displacement Reactions of Allylic Compounds: Stereo- (List continued on next page.)

OTHER PUBLICATIONS and Regiochemistry," *Tetrahedron*, 36, 1901–1930 (1980).

P. Markov et al., "Reactions of Calcium and Magnesium Naphthalenides with Ethyl Esters of 2-Bromopropionic and 2-Bromobutyric Acid in Liquid Ammonia," *J. Organomet. Chem.*, 81, 1–6 (1974).

P, Markov et al., "Über die Reaktion von Biphenyl mit Magnesium in flüssigem Ammoniak," *Monatshefte fur Chemie*, 107, 619–624 (1976) (with English language abstract).

M. J. McCormick et al., "Preparation of Activated Calcium, Strontium, and Barium Powders by Reduction of Alkaline Earth Di-iodides," *J.C.S., Chem. Commun.*, 778–779 (1990).

Y. Nakano et al., "On the Reaction Between Magnesium and Iosprene," *Tetrahedron Lett.*, 28, 2833–2836 (1972).

E. Negishi, "Bimetallic Catalytic Systems Containing Ti, Zr, Ni, and Pd. Their Applications to Selective Organic Syntheses," *Pure & Appl. Chem.*, 53, 2333–2356 (1981).

R. A. O'Brien et al., "Direct Metalation of p-Bromopolystyrene Using Highly Reactive Copper and Prepation and Reaction of Highly Reactive Copper Bound to an Insoluble Polymer," *J. Org. Chem.*, 55, 788–90 (1990).

R. A. O'Brien et al., "Chemical Modification of Halogenated Polystyrene Resins Utilizing Highly Reactive Calcium and the Formation of Calcium Cuprate Reagents in the Preparation of Functionalized Polymers," *J. Org. Chem.*, 57, 2667–2677 (1992).

R. A. O'Brien et al., "Functionalization of Halogenated Polystyrene Resins Utilizing Highly Reactive Calcium," *J. Inorg. & Organomet. Poly.*, 2, 345–356 (1992).

R. A. O'Brien, "Chemical Modification of Halogenated Polystyrene Resins Utilizing Highly Reactive Copper and Calcium and the Chemistry of Highly Reactive Copper Contained in a Polymer", Abstract of Ph.D. Thesis (1992), The University of Nebraska.

G. H. Osborn; *Synthetic Ion-Exchangers; The Macmillan Co.: New York, N.Y. (1956); pp. 32–33.*

W. J. Richter, "Diorganosilacyclopent-3-ene Derivatives from Diorganodichlorosilanes and Butadienemagnesium: Evidence for Crotyl-Grignard Intermediates," *J. Organomet. Chem.*, 289, 45–49 (1985).

R. D. Rieke, "New synthetic methods using highly reactive metals," Abstract of National Institute of Health Grant No. GM35153 obtained from the online DIALOG file Federal Research in Progress (1992).

R. D. Rieke et al., "Activated Metals. I. Preparation of Highly Reactive Magnesium Metal," *J. Am. Chem. Soc.*, 94, 7178–7179 (1972).

R. D. Rieke et al., "Acitvated Metals. The Effect of Added Metal Salts on Magnesium Reactivity," *J.C.S. Chem. Comm.*, 879–880 (1973).

R. D. Rieke et al., "Activated Metals. IV. Preparation and Reactions of Highly Reactive Magnesium Metal," *JACS*, 96, 1775–1781 (1974).

R. D. Rieke, "Use of Activated Metals in Organic and Organometallic Synthesis," i Top. Curr. Chem., 59, 1–31 (1975).

R. D. Rieke, "Preparation of Highly Reactive Metal Powders and Their Use in Organic and Organometallic Synthesis," *Acc. CHem. Res.*, 10, 301–306 (1977).

R. D. Rieke, "Preparation and Study of Highly Reactive Metal Powders," *U.S. NTIS, AD Rep.*, Number: AD-A150026, pp. 1–18 (1978) (Citation: Gov. Rep. Announce. Index (U.S.) 1978, 78(1), 171).

R. D. Rieke et al., "Preparation of Highly Reactive Metal Powders. A New Procedure for the Preparation of Highly Reactive Zinc and Magnesium Metal Powders," *J. Org. Chem.*, 46, 4323–4324 (1981).

R. D. Rieke, "Studies on Unusually Reactive Metal Powders. Preparation of New Organometallic and Organic Compounds Including Potential New Catalysts," *Report*, Number: DOE/ER/10603–T3; Order No. DE85014844, 18 pages (1985) (Citation: Energy Res. Abstr. (1985) 10(18), Abstr. No. 37255).

R. D. Rieke et al., "Preparation of Highly Reactive Metal Powders. Some of Their Uses in Organic and Organometallic Synthesis," *ACS Symposium Series*, 333, 223–245 (1987).

R. D. Rieke, "Preparation of Organometallic Compounds from Highly Reactive Metal Powders," *Science*, 246, 1260–1264 (1989).

R. D. Rieke et al., "New Organocopper Reagents Prepared Utilizing Highly Reactive Copper," *Tetrahedron*, 45, 443–454 (1989).

R. D. Rieke "Preparation of Highly Reactive Pow- (List continued on next page.)

OTHER PUBLICATIONS ders/Surfaces and Their Use in the Preparation of Organometallic Compounds," *Crit. Rev. Surf. Chem.*, 1, 131–166 (1991).

R. D. Rieke et al., "Chemistry of Substituted (2-Butene-1,4-diyl)magnesium: A Facile Approach to Complex Carbocycles, Functionalized Ketones and Alcohols and Silicon-Containing Heterocycles," *J. Org. Chem.*, 56, 3109–3118 (1991).

R. D. Rieke et al., "One-Step Spiroannulation Using 1,2-Bis(methylene) Cycloalkane-Magnesium Reagents," *J. Org. Chem.*, 57, 6560–6565 (1992).

R. G. Salomon, "A Facile One-Step Synthesis of 5-Silaspiro[4.4]nona-2,7-diene," *J. Org. Chem.*, 39, 3602 (1974).

F. K. Signalgo et al., "The Preparation of Some Mono- and Dialkylcyclohexanes," *J. Am. Chem. Soc.*, 55, 3326–3332 (1933).

J. M. Tour et al., "Facile Li/HMPA-Promoted Polymerization Method for the Synthesis of Soluble Poly(phenylenes)," *J. Am. Chem. Soc.*, 113, 2309–2311 (1991).

M. Ueda et al., "Synthesis of Poly(3-phenyl-2,5-thiophene) by Nickel-Catalyzed Coupling Polymerization of 3-Phenyl-2,5-dichlorothiophene," *Macromolecules*, 24, 2694–2697 (1991).

M. Vandewalle et al., "Total Synthesis of Polycarbocyclic Sesquiterpenes," *Tetrahedron*, 41, 1767–1831 (1985).

D. Walther et al., "Neue Bausteine metallorganischer Synthesen: 'Magnesium-dien'—Vergindungen," *Naturwiss. Reihe.*, 34, 789 (1985) with English language abstract D. Walther et al., "New synthons for organometallic synthesis: magnesium-diene compounds," *Chem. Abs.*, 105, 746 (Abstract No. 105:42862z) (1986).

R. M. Wehmeyer et al., "Direct Formation of Functionalized Ketones via the Coupling of Functionalized Organocopper Reagents with Acid Chlorides," *Tetrahedron Lett.*, 29, 4513–4516 (1988).

P. A. Wender et al., "Organobiscuprates): A New Class of Reagents and Method for Spiroannelation," *J. Am. Chem. Soc.*, 110, 2218–2223 (1988).

T.—C. Wu et al., "Organocalcium Chemistry: Preparation and Reactions of Highly Reactive Calcium," *J. Org. Chem.*, 55, 5045–5051 (1990).

H. Xiong et al., "Facile Formation of Substituted 2-Butene-1,4-diylmagnesium Using Highly Reactive Magnesium: A Simple Approach to Complex Carbocycles and Functionalized Ketones," *J. Org. Chem.*, 54, 3247–3252 (1989).

H. Xiong et al., "The Magnesium Complexes of 1,2-Dimethylenecycloalkanes: A New Method for a One-Step Spiroannelation," *Tetrahedron Lett.*, 32, 5269–5272 (1991).

H. Xiong et al., "Reactions of Magnesium Complexes of 1,2-Bis(methylene)cycloalkanes with Carboxylic Esters: The Formation of a Versatile Intermediate Capable of Generating Fused Rings or, —Unsaturated Ketones," *J. Am. Chem. Soc.*, 114, 4415–4417 (1992).

H. Xiong et al., "Synthesis of Spiro —Lactones from Conjugated Dienes," *J. Org. Chem.*, 57, 7007–7008 (1992).

T. Yamamoto et al., "A Novel Type of Polycondensation Utilizing Transition Metal-Catalyzed C—C Coupling. I. Preparation of Thermostable Polyphenylene Type Polymers," *Bull. Chem. Soc. Japan*, 51, 2091–2097 (1978).

T. Yamamoto et al., "Preparation and Characterization of Poly(thienylene)s," *Bull. Chem. Soc. Jpn.*, 56, 1497–1502 (1983).

H. Xiong "Chemistry of Conjugated Diene-Magnesium Reagents: A Novel Approach to Cyclic and Functionalized Molecules", Abstract of Ph.D. Thesis (1992), The University of Nebraska.

T. Yamamoto et al., "Nickel and palladium catalyzed dehalogenating polycondensation of dihaloaromatic compounds with zinc. A new route to poly(2,5--thienylene)s and poly(1,4-phenylene)," *Makromol. Chem., Rapid Communications*, 6, 671–674 (1985).

M. Yang et al., "The Preparation and Some Reactions of Isoprene-Magnesium Compound," *Tetrahedron Lett.*, 44, 3843–3846 (1970).

H. Yasuda et al., "Unique Chemical Behavior and Bonding of Early-Transition-Metal-Diene Complexes," *Acc. Chem. Res.*, 18, 120–126 (1985).

H. Yasuda et al., 37 New Aspects of Carbanion Chemistry. Structure of Pentadienyl Anions and Butenediyl Dianions and Their Roles in Organic and Inorganic Syntheses," *Recent Advances in Anionic Polymerization*, 59–71 (1987).

M. C. P. Yeh et al., "2-Cyanoethylzinc Iodide: A new Reagent with Reactivity Umpolung," *Tetrahedron Lett.*, 29, 2395–2396 (1988).

S. H. Yu et al., "Preparation of Alkylmagnesium Fluorides," *J. Org. Chem.*, 36, 2123–2128 (1971).

SOLUBLE HIGHLY REACTIVE FORM OF CALCIUM AND REAGENTS THEREOF

GOVERNMENT SUPPORT

The present invention was made with government support under Contract No. GM35153 awarded by the National Institute of Health. The Government has certain rights in this invention.

This is a continuation of application Ser. No. 08/062,135, filed May 17, 1993, now abandoned, which is a continuation-in-part of application Ser. No. 07/738,828, filed Aug. 1, 1991, now U.S. Pat. No. 5,211,889 which is incorporated herein by reference.

BACKGROUND OF THE INVENTION

Organocalcium reagents are highly desirable reagents for organic synthesis. They possess many attributes that are distinct from organomagnesium and other organometallic reagents. For example, they often react stereoselectively and regioselectively. Furthermore, they do not possess the extreme nucleophilicity of such reagents as Grignard reagents. Consequently, organocalcium reagents can generate distinctly different chemistry from that of other organometallic reagents.

The development of organocalcium chemistry has been slow with respect to extensive studies of organometallic reagents of other light metals, such as magnesium. The neglect of organocalcium chemistry has been due, at least in part, to the lack of a facile method of preparing the organocalcium compounds. Furthermore, the few dialkyls and alkyl halides of calcium studied in the early to mid-1900's proved to be thermally unstable, generally insoluble, and difficult to manipulate.

Another impediment to the development of organocalcium chemistry has been the expectation that calcium and organocalcium compounds should parallel that of their magnesium analogs. In fact, calcium is known to more closely resemble sodium rather than magnesium in its chemical reactivity, although calcium is somewhat less reactive than sodium. For example, unlike magnesium but much like sodium, calcium is known to be an excellent reducing agent. Furthermore, unlike magnesium, calcium is soluble in liquid ammonia giving a blue solution similar to the solutions of the Group I metals, which are believed to be solvated metal ions and electrons.

Although there is little known about organocalcium compounds, direct oxidative addition of organic substrates to bulk calcium metal, suspended in a suitable solvent, has traditionally been the method of forming organocalcium compounds. This has been limited, however, by the reduced reactivity of the bulk calcium metal. Although it is not entirely clear, this is presumably due to surface poisoning factors.

Thus, developments in the production of organocalcium compounds have centered around activating the bulk calcium metal. Typically, this has involved alloying of the bulk metal, the addition of activating agents to a reaction mixture, or the use of highly purified bulk metal. For example, Ca amalgam or Ca-Mg alloys have been used to activate the Ca metal to oxidative addition reactions. Iodine has also been used as an activating agent in a reaction mixture.

Although there are several procedures known for the reduction of metal salts to metal powders reactive towards oxidative addition, each metal typically requires unique permutations of the procedures to obtain a reactive species. That is, there is no standardized approach that can produce metal powders of identical, or even similar, reactivity. For example, magnesium metal in the form of a black powder can be obtained by reducing magnesium salts in an ethereal solvent with molten sodium or potassium; however, the use of an alkali metal in conjunction with an electron carrier such as naphthalene can produce magnesium powder of even greater reactivity. These procedures can produce finely divided highly reactive metal powders; however, these procedures are not standardized or generalized.

The organocalcium derivatives RCaX are typically most readily formed when X=I; however, the preparation of RCaX (X=Br, Cl) usually requires activated calcium. Even with activated, or highly pure calcium, few examples of organocalcium halides, or other organocalcium reagents, have actually been prepared. Typically, of the reagents prepared, the overall yields are generally low. Although simple primary and secondary alkyl iodides have been shown to react with highly pure calcium, i.e., Ca containing less than 0.5% Mg and 0.002% Na, in reasonable yields, the tertiary alkyliodocalcium compounds have proven to be very difficult to prepare. In fact, most tertiary alkyls are generally formed in only trace amounts.

Therefore, an object of the invention is to produce a calcium species that is more reactive than those obtained from traditional methods. Another object of the invention is to produce a calcium species that is soluble and highly reactive towards oxidative addition. Yet another object of the invention is the direct production of a wide variety of organocalcium compounds, e.g., aryl and alkyl calcium compounds, particularly tertiary alkyl calcium compounds. Furthermore, an object of the invention is the synthesis of new organic compounds or the synthesis of known organic compounds using more effective and/or more direct synthetic methods.

SUMMARY OF THE INVENTION

These and other objects are achieved by the present invention which is directed to the use of a soluble highly reactive calcium species to form new organocalcium reagents and to synthetic reactions performed with these organocalcium reagents. As used herein, the phrase "highly reactive" refers to the reactivity of the calcium species in organic reactions, particularly oxidative addition reactions. A calcium species is highly reactive if it reacts with a wide variety of primary, secondary, and particularly tertiary alkyl halides in relatively high yields, for example in greater than about 50% yields, preferably in greater than about 70% yields.

The soluble highly reactive calcium species is composed of formally zerovalent calcium metal atoms in combination or complexation with a solubilizing agent in an ethereal, polyethereal, or hydrocarbon solvent. The solubilizing agent can be any of a variety of macrocyclic polyethers, cryptates, or polyenes capable of interacting with the formally zerovalent calcium metal atoms in such a manner that a less reactive finely divided powder does not substantially precipitate out of solution. Preferably, the solubilizing agent is a polyene. More preferably, the solubilizing agent is an aromatic polyene, i.e., an arene or polyarylene, such as an aromatic electron-transfer compound. Examples of aromatic electron-transfer compounds include biphenyl, naphthalene, and anthracene. The soluble highly reactive calcium species can also be in combination with an alkali metal salt.

The soluble highly reactive calcium species is formed from the reduction of a calcium(II) salt, preferably a soluble calcium(II) salt, the counterion of which can be any of a variety of anions without an acidic proton. For example, the anion can be a sulfate, nitrate, nitrite, cyanide, or halide. Preferably, the anion is a cyanide or a halide, and most preferably a halide. Of the halides, the most effective counterion is a bromide or iodide.

The solubilizing agent is from a solubilized reducing agent that is capable of reducing calcium(II) salts in an ethereal, polyethereal, or hydrocarbon solvent. A reducing agent with a reduction potential of about $-1.5$ volts or more negative is acceptable. Preferably, the reducing agent has a reduction potential of about $-1.8$ volts or more negative, and most preferably about $-2.0$ volts or more negative. Examples of such reducing agents include alkali metal salts of aromatic anions. Examples of preferred reducing agents include sodium, potassium, cesium, or lithium naphthalenide, biphenylide, or anthracenide. Other examples of preferred reducing agents include alkali metal-polyether solvates, alkali metal-crown ether solvates, alkali metal-cryptate solvates, etc.

Typically, the reduction of the calcium(II) salt is carried out in an ethereal, polyethereal, or hydrocarbon solvent. These include, but are not limited to, ethyl ether, tetrahydrofuran, glyme, diglyme, triglyme, benzene, and the like. If a hydrocarbon solvent is used, it preferably contains a secondary solubilizing agent such as N,N,N',N'-tetramethylethylenediamine (TMEDA) to assist in solubilizing the starting materials and product, but particularly the starting materials. Preferably, the reaction is carried out in an ethereal or polyethereal solvent. More preferably, it is carried out in tetrahydrofuran (THF).

The organocalcium reagents of the present invention are prepared from the soluble highly reactive calcium species produced as described above and an organic compound. The organic radical of the organocalcium reagent can be an aliphatic, aryl, arylalkyl, heterocyclic or polymeric group. The aliphatic, aryl, arylalkyl or polymeric group of this reagent may optionally be functionalized with such groups as allyls or ethers.

The organocalcium reagent can also contain one or more halide groups (herein referred to as organocalcium halides). However, this is not necessarily a requirement for the use of organocalcium reagents in organic synthesis. For example, if the organic compound reactant contains a 1,3-diene functionality or other conjugated polyunsaturated functionality, no halide is generally present. Thus, the organocalcium reagent does not necessarily contain a halide group.

In the context of this invention, the term "aliphatic" means a saturated or unsaturated linear, branched, or cyclic hydrocarbon radical. The term "alkyl" means a saturated linear, branched, or cyclic hydrocarbon radical. The term "heterocyclic" means a mono- or polynuclear cyclic radical containing carbons and one or more heteroatoms such as nitrogen, oxygen, or sulfur or a combination thereof in the ring or rings, including but not limited to pyridine, pyrrole, indole, thiazole, pyrazine, guanine, cytosine, thymine, adenine, uredine, uracil, oxazole, pyrazole, hydantoin, piperazine, quinoline, xanthene, 1,10-phenanthroline, and acridine. The term "aryl" means a mono- or polynuclear aromatic hydrocarbon radical. The term "arylalkyl" means a linear, branched, or cyclic alkyl hydrocarbon radical having a mono- or polynuclear aromatic hydrocarbon or heterocyclic substituent.

The term "polymeric" or "polymer" is used herein in its most general sense to mean a compound consisting essentially of repeating structural units. It refers to inorganic polymers such as silica and alumina. It also refers to organic polymers such as polyolefins, polystyrenes, polyesters, polyurethanes, polyamides, polycarbonates, polyethers, etc.

The organocalcium reagents of the present invention can be used in a variety of organic synthetic reactions. For example, the organocalcium halide reagents react in a Grignard-type fashion to form alcohols from aldehydes and ketones. They also react with copper(I) salts to form organocalcium cuprates, which can further react with enones and acid chlorides. Organocalcium dihalides can be used in the preparation of novel polymeric materials, such as two-dimensional linear polymers.

The present invention is also directed to a method for the preparation of spirocycles, γ-lactones, particularly spiro γ-lactones, δ-lactones, including spiro δ-lactones, γ-lactams, and chiral vicinal diols. These compounds can be prepared from calcium complexes of 1,3-dienes that are prepared from the highly reactive calcium of the present invention. For example, the preparation of a γ-lactone includes the steps of: contacting a calcium(II) salt in an ethereal, polyethereal, or hydrocarbon solvent with a reducing agent having a reduction potential of about $-1.5$ volts, or more negative, relative to SCE, to form a highly reactive calcium species; contacting the highly reactive calcium species with a conjugated diene to form a 2-butene-1,4-diylcalcium complex; contacting the 2-butene-1,4-diylcalcium complex with a ketone or aldehyde in an ethereal, polyethereal, or hydrocarbon solvent to form a 1,2-addition adduct resulting from the incorporation of one molecule of the ketone or aldehyde into the 2-butene-1,4-diylcalcium complex; contacting the 1,2-addition adduct with carbon dioxide to form a nucleophilic addition product; and contacting the nucleophilic addition product with an aqueous acid to form a γ-lactone, preferably a spiro γ-lactone. The conjugated diene can be a cyclic hydrocarbon containing at least two conjugated exocyclic double bonds or an open-chain conjugated diene, such as 2,3-dimethyl-1,3-butadiene. The ketone and aldehyde can be any aryl or alkyl ketone or aldehyde including those containing heteroatoms, such as nitrogen. For example, the ketone can be any cyclic ketone such as cyclohexanone to yield a spiro γ-lactone, or it can be an acyclic ketone to yield a γ-lactone. Any alkyl or aryl aldehyde would yield a γ-lactone.

DETAILED DESCRIPTION OF THE PRESENT INVENTION

The present invention is based upon the discovery that a highly reactive soluble calcium metal species displays surprising and unexpected reactivity and usefulness in organic synthetic procedures. For example, the highly reactive soluble calcium species displays surprising and unexpected reactivity toward a wide variety of aliphatic, aryl, heterocyclic, arylalkyl and polymeric compounds, particularly compounds containing one or more halide atoms (hereinafter organic halides), or compounds containing a 1,3-diene functionality or conjugated polyunsaturation.

The Calcium Species

The soluble highly reactive calcium species is composed of formally zerovalent calcium metal atoms in combination or complexation with a solubilizing agent. By "formally zerovalent" it is meant that the formal oxidation state, or charge, is equal to the group number (i.e., 2) minus the number of unshared electrons (i.e., 2) minus the number of bonds (i.e., 0).

The solubilizing agent that is in combination or complexation with the formally zerovalent calcium species of the present invention preferably comes from a corresponding solubilized reducing agent that is capable of reducing Ca(II) salts in an ethereal, polyethereal, or hydrocarbon solvent. The solubilizing agent can be any of a variety of macrocyclic polyethers, cryptates, or polyenes, and the like, capable of interacting with the formally zerovalent calcium metal atoms in such a manner that a less reactive finely divided powder does not precipitate out of solution to any significant extent. By this it is meant that the formally zerovalent calcium species of the present invention is substantially completely soluble in a ethereal, polyethereal, or hydrocarbon solvent with only about 20% or less of the calcium species in a solid state, i.e., a state without any significant interaction with the solubilizing agent.

Preferably, the solubilizing agent is a polyene. More preferably, the solubilizing agent is an aromatic polyene, i.e., an arene or polyarylene, such as an aromatic electron-transfer compound. Examples of aromatic electron-transfer compounds include but are not limited to, biphenyl, naphthalene, and anthracene. Compounds such as these are typically capable of transferring electrons in an oxidation reduction reaction through the formation of radical anions.

Thus, in a preferred embodiment, the highly reactive calcium species of the present invention is composed of zerovalent calcium metal atoms in combination or complexation with one or more of the arenes naphthalene, anthracene, or biphenyl. More preferably, the highly reactive calcium species of the present invention is composed of zerovalent calcium metal atoms in combination or complexation with the arene biphenyl.

The highly reactive calcium species of the present invention, whether in a mixture or complex, is soluble in ethereal, polyethereal, or hydrocarbon solvents. These include, but are not limited to, ethyl ether, tetrahydrofuran, glyme, diglyme, triglyme, benzene, and the like. If a hydrocarbon solvent is used, it preferably contains a secondary solubilizing agent such as N,N,N',N'-tetramethylethylenediamine, or other diamine or bidentate ligand capable of solubilizing the starting materials and product, particularly the starting materials.

The soluble highly reactive calcium species can also be in combination with an alkali metal salt wherein the anion does not contain an acidic proton. The alkali metal of the salt can be Li, Na, K, Rb, or Cs. Preferably, it is Li, Na, or K, and most preferably it is Li. The anion can be, but is not limited to, a nitrate, nitrite, sulfate, cyanide, and/or halide. Preferably, the anion is a halide or cyanide. More preferably, the anion is a halide. Most preferably, the anion is bromide or iodide.

The most specific and preferred embodiment of the soluble highly reactive calcium species of the present invention is composed of zerovalent calcium metal atoms in combination with, or complexed with, biphenyl and a lithium halide. The solvent used to solubilize the most preferred embodiment of the calcium species is tetrahydrofuran (THF).

The soluble highly reactive calcium species of the present invention is prepared from the reduction of a calcium(II) salt, the counterion of which can be any of a variety of anions that does not contain an acidic proton. For example, the anion can be a sulfate, nitrate, nitrite, cyanide, or halide. Preferably, the anion is a cyanide or a halide. More preferably, the anion is F, Cl, Br, or I. Most preferably the anion of the Ca(II) salt is Br or I.

Generally, the reducing agent can be any solubilized reducing agent that is capable of reducing Ca(II) salts in an ethereal, polyethereal, or hydrocarbon solvent. Any reducing agent having a reduction potential of about −1.5 volts or more negative, relative to the standard calomel electrode (SCE), will satisfy this relation. It is preferred, however, if the reducing agent has a reduction potential of about −1.8 volts or more negative, and most preferred if the reducing agent has a reduction potential of about −2.0 volts or more negative. Preferably, the reduction takes place in an ethereal or polyethereal solvent, and more preferably in tetrahydrofuran.

Examples of suitable solubilized reducing agents include alkali metal salts of aromatic anions, such salts being, for instance, sodium or lithium naphthalenide, anthracenide, or biphenylide; alkali metal-polyether solvates; alkali metal-crown ether solvates; alkali metal-cryptate solvates, etc. Preferably, the reducing agent is an alkali metal arene salt. More preferably, the reducing agent is a combination of an alkali metal cation and an anion of an aromatic electron transfer compound, such as biphenyl, anthracene, or naphthalene. Most preferably, the reducing agent is preformed. Of the preformed alkali metal arene salts, the most preferred is lithium biphenylide.

By "preformed" it is meant that the alkali metal and about 1–1.2 equivalents of the arene are allowed to react substantially completely, i.e., until substantially all the alkali metal is consumed, before contacting any calcium salts. The formation of the preformed reducing agent typically takes place in an ethereal, polyetheral, or hydrocarbon solvent, and generally is substantially complete in about 2 hours.

Because the soluble highly reactive calcium species is preferably utilized within a short period of time after its preparation, it can also contain the alkali metal salt produced from the cation of the aromatic reducing agent and the anion of the calcium salt starting material. Generally, the alkali metal salt is not believed to effect the reactivity of the soluble highly reactive calcium; however, it may facilitate the reactivity of the organic compounds, particularly the oxidative addition reaction with the organic halides.

The process for reduction to produce the soluble highly reactive calcium species of the present invention is conducted under conditions designed to prevent its reoxidation and substantial precipitation as calcium powder. Generally, these conditions include use of ethereal, polyethereal, or hydrocarbon solvents and the exclusion of oxygen. Also, the conditions are controlled so as to promote the existence of the calcium atoms as small soluble clusters and to avoid their agglomeration into larger configurations that could precipitate out of solution. Larger clusters of metal atoms generally means lower solubility and lower reactivity.

Preferably, these conditions include temperatures of about 100° C. or less, an inert atmosphere, e.g., an argon or nitrogen atmosphere, a reaction time of about 1 hour, and an ether or polyether solvent such as diethyl ether, dimethyl ether, tetrahydrofuran and the like, or a hydrocarbon solvent. The Ca(II) salt can be soluble in the solvent of the reaction, or it can be a suspension therein. The Ca(II) salt is preferably soluble in the solvent at room temperature, as is the resultant soluble highly reactive calcium species. The reduction can as well be conducted in a hydrocarbon solvent with N,N,N',N'-tetramethylethylenediamine (TMEDA) to solubilize or disperse the starting material complex and reducing agent. Typically, the molar ratio of the reducing agent to the Ca(II) salt is about 2:1 for an equivalent amount; however, the Ca(II) salt can be in excess. Preferably, the Ca(II) salt is present in an amount of about 1.1–2.0 equivalents, and more preferably in an amount of about 1.5–2.0 equivalents, per equivalent of reducing agent. Excess Ca(II) salt is used to ensure there is little or no reducing agent present to interfere with subsequent reactions, particularly if the highly reactive calcium species is used without isolation.

Although the soluble calcium species can be maintained for a time under these conditions, it is also quite reactive. Consequently, it is preferably synthesized and used immediately or within a very short period of time. However, it can be stored for several days and much longer at lower temperatures under an inert atmosphere.

The formal oxidation state of the calcium metal in the preferred highly reactive calcium species is considered to be zero; however, it is believed that the calcium arene, e.g., calcium biphenyl complex, has considerable charge transfer between the calcium and the arene. Thus, the calcium species can exist as a tight ion pair, or as a complex with significant charge transfer, between the calcium atoms and the anion. In contrast, it is believed that in solvents such as liquid ammonia, the Ca(II) ions are uninvolved ions in any reaction. With the soluble highly reactive calcium complex of the present invention, however, it is believed that the calcium ions are tightly bound and play an intimate role in the electron transfer process.

Notwithstanding these theoretical considerations, the soluble calcium species of this invention will react with organic halides and 1,3-diene compounds, for example, to produce selectively reactive organocalcium compounds. The organocalcium species undergo a variety of reactions to produce both novel organic compounds and novel synthetic methods for known organic compounds.

The Organocalcium Reagents

The soluble highly reactive calcium species of the present invention reacts readily with a wide variety of substrates to generate excellent yields of organocalcium reagents, which can be used to produce unique organic compounds or known organic compounds from unique synthetic routes. Generally, the organocalcium reagents of this invention are composed of an aliphatic, aryl, heterocyclic, arylalkyl or polymeric organic radical in combination with calcium atoms derived from the foregoing soluble highly reactive calcium species. These organocalcium compounds can be monomeric or polymeric.

Preferably, the organocalcium reagents of this invention are mixtures or combinations of the organocalcium compounds and alkali metal salts. With respect to these mixtures or combinations it is believed the calcium moiety or moieties of the organocalcium compounds associate in some manner with alkali metal salts present to form the organocalcium reagent. It is further believed that this association is in part responsible for the novel and selective reactivity of certain of the organocalcium reagents of this invention, although this is not intended to be limiting.

The organocalcium reagents are produced by reaction of the highly reactive calcium species, prepared as described above, with an aliphatic, aryl, heterocyclic, arylalkyl, or polymeric compound. Preferably, these organic starting materials have one or more halide groups. If the aliphatic, aryl, arylalkyl, heterocyclic, or polymeric compound contains a 1,3-diene or polyunsaturation functionality, no halide is generally required for reactivity.

The reactions are generally conducted under conditions designed to preserve the integrity of the organocalcium reagents, those conditions include, for example, the exclusion of water and oxygen. Preferably the reactions are carried out in an ethereal, polyethereal, or hydrocarbon solvent. More preferably, the are carried out in an ethereal or polyethereal solvent. Most preferably they are carried out in tetrahydrofuran (THF).

Preferably, the conditions also include temperatures of less than about 100° C. Alkyl halides typically react with the soluble highly reactive calcium at temperatures between about −140° C. and about 100° C., preferably between about −80° C. and about 35° C. Aryl halides react with the soluble highly reactive calcium at temperatures between about −80° C. and about 100° C., preferably between about −30° C. and about 30° C. Organic compounds containing a 1,3-diene functionality react with the soluble highly reactive calcium at temperatures between about −140° C. and about 100° C., preferably between about −30° C. and about 30° C. Typical yields of the organocalcium reagents are greater than about 50%, and preferably greater than about 70%. In some instances the organocalcium reagents can be produced in nearly quantitative yields.

The organocalcium reagents are typically prepared in the same medium used to produce the highly reactive calcium species. The highly reactive calcium species is preferably present in an equimolar ratio with the organic compound, i.e., about 1 mole calcium to 1 mole reactive organic compound. More preferably, the calcium is present in an excess amount, e.g., about 1.1–2.0 moles calcium to 1 mole reactive organic compound.

Generally, the organic group of the organocalcium reagent can be any saturated, olefinically unsaturated or aromatic hydrocarbon or a heterocycle containing carbon, nitrogen, oxygen, sulfur, phosphorous or combinations thereof in the heteronucleus. Examples of organic compounds that react with the highly reactive calcium species of the present invention include, but are not limited to, 1-bromooctane, 1-chlorooctane, 1-bromo-3-phenoxypropane, 1-bromo-5phenoxypentane, bromocyclohexane, 1-bromoadamantane, m-bromotoluene, m-bromoanisole, p-chlorotoluene, fluorobenzene, 1,4-diphenyl-1,3-butadiene, 2,3-dimethyl-1,3-butadiene, 1,4-dibromobenzene, and 2,5-dibromothiophene.

The molecular size of the organocalcium reagents can range from organic compounds and monomers, typically having from 1 to about 300 carbons, to polymeric compounds having molecular weights up to and including the million range. Preferred aliphatic, aryl, heterocyclic, and arylalkyl groups include linear or branched alkyl, cycloalkyl, allyl, vinyl, phenyl, benzyl, pyridyl, quinolinyl, piperadinyl, cytosinyl, uracinyl, guaninyl, adenosinyl, pyrrolyl, thiazolyl, the methylenyl derivatives of such heterocycles and phenyl alkyl groups as well as the hydrocarbon substituted and/or functionalized forms thereof. The hydrocarbon substituents can be one or more of such groups as alkyl, cycloalkyl, heterocyclic, olefinic and aromatic groups as well as combinations thereof, each substituent having from 1 to about 30 carbons. The hydrocarbons can be optionally functionalized with such groups as allyls, ethers, esters, nitriles, amides, and ketones.

Although the organocalcium reagents can be functionalized as outlined above with groups such as allyls, ethers, esters, nitriles, amides, and ketones, they will maintain a stable state and will typically not self-react to a significant extent as long as they are maintained within the appropriate low temperature range. At higher temperatures, however, the organocalcium species can self-react, but if they are modified by reaction with Cu(I) salts to yield derivatives of organocalcium reagents, i.e., organocalcium cuprates as discussed below, synthetic chemistry can be carried out with the more highly functionalized organocalcium species.

Reactivity of the Organocalcium Reagents

In general, the organocalcium reagents undergo coupling reactions with organic electrophiles, i.e., compounds that are deficient in electrons, such as acid chlorides, ketones, aldehydes, nitriles, esters, amides, $\alpha,\beta$-unsaturated carbonyl compounds, epoxides, and the like. Specific illustrations of the novel utility of the soluble highly reactive calcium species of the present invention and the organocalcium reagents produced from the soluble highly reactive calcium are described below. In certain situations the organocalcium reagents can also react with copper(I) salts to produce organocalcium reagents containing copper atoms, herein referred to as organocalcium cuprate reagents, which possess unique reactivity patterns.

Generally, the coupling reactions between the organocalcium reagent and the organic electrophile are typically conducted in the same medium used to produce the organocalcium reagent. The reaction is conducted under conditions designed to favor the production of the desired coupled product. Those conditions generally include low temperature, use of appropriate electrophiles, addition of the electrophile to the organocalcium reagent and stirring with appropriate reaction times. One or more of these conditions will be appropriate for use in particular instances. Choice of some or all of them is within the ordinary artisan's skill.

Preferably, the reactions are carried out in an ethereal, polyethereal, or hydrocarbon solvent such as ethyl ether, tetrahydrofuran, glyme, diglyme, triglyme, benzene, and the like. If a hydrocarbon solvent is used, it preferably contains a secondary solubilizing agent such as N,N,N',N'-tetramethylethylenediamine, or the like. More preferably, the reactions are carried out in an ethereal or polyethereal solvent. Highly solvating solvents, such as THF, glyme, diglyme, and triglyme, facilitate the oxidative addition reactions with the organic halides and facilitate complex formation with 1,3-dienes.

Residual alkali metal halide, e.g., lithium halide, is preferably present in the reaction mixture of the electrophiles and the organocalcium reagents. Although not intended to be limited by any theory, it is believed that the excess alkali metal halide facilitates electron transfer to the organic halide and 1,3-dienes in some manner.

The reagents and reactions of this invention are useful in the organic synthesis of organic compounds that are difficult or impossible to prepare by other techniques. In particular, the facility to react aryl chlorides and fluorides at low temperatures, the ability to prepare tertiary organocalcium reagents, and the ability to modify the chemical reactivity by formation of a calcium cuprate, are all useful for designing organic synthetic procedures. As a result, these unique capabilities promote the use of the reagents and reactions of this invention in the organic synthesis of pharmaceutical compounds, insecticides, herbicides, polymeric compounds, organic additives for polymer compositions, organic conductors, and organic information storage devices. Specific examples include the syntheses of two-dimensional polymers, prostaglandins, penicillins, tranquilizers, and carbocyclic anticancer agents. These syntheses are made more efficient, are economically feasible, and, in several cases, represent the only route possible. They open the synthetic and investigatory arenas to the development and use of rare or previously unavailable organic compounds.

Grignard-Type Reactions with Highly Reactive Calcium

As stated above, the highly reactive calcium species of the present invention reacts readily with a wide variety of substrates to generate excellent yields of organocalcium reagents, which can be used in a wide variety of synthetic preparations. For example, the organocalcium reagents, prepared directly from the soluble highly reactive calcium species and organic halides, efficiently undergo Grignard-type reactions. Example 2 and Table I summarize some specific examples of 1,2-addition reactions with cyclohexanone utilizing the soluble highly reactive calcium species of the present invention.

Traditional Grignard reactions involve the 1,2-addition of RCaX to aldehydes to form alcohols. Prior to the present developments with the soluble highly reactive calcium species, the preparation of RCaX reagents, i.e., organocalcium halides, has been limited. Thus, the development of synthetic procedures, such as Grignard-type reactions, has been limited. The present RCaX reagents undergo 1,2-addition reactions to the carbonyl groups of aldehydes and ketones, for example, under typical Grignard reaction conditions, to form alcohols in yields greater than about 50%, preferably greater than about 70%.

Any of the organocalcium halide reagents, containing one or more halide atoms, discussed above can be used in Grignard-type 1,2-addition reactions. Furthermore, any of a variety of aldehyde, ketones, esters, amides, and nitriles can be used effectively in the 1,2-addition reactions.

Significantly, the organocalcium halide reagents of the present invention can be used to prepare tertiary organocalcium reagents. For example, the Grignard-type reaction for 1-bromoadamantane utilizing the soluble highly reactive calcium affords 1-(1-adamantyl)cyclohexanol in 80% yield. The direct reaction of 1-bromoadamantane with metals is well known to yield mainly reductive cleavage or dimerization. Accordingly, this method represents a significant new approach to the preparation of 1-metalloadamantane. More importantly, use of the active calcium represents a general route to tertiary organocalcium reagents.

The Grignard-type reactions are carried out under conditions designed to produce high yields, i.e., yields greater than about 50%, and preferably greater than about 70%, of the resultant alcohols. These conditions include the exclusion of oxygen and temperatures of less than about 100° C., preferably between about −140° C. and about 100° C., and more preferably between about −80° C. and about 100° C.

Preparation and Reactions of Organocalcium Cuprate Reagents

While a wide spectrum of different metal cuprates are known, calcium cuprates are not generally known. Addition of copper(I) salts to the organocalcium reagents described above result in new organocalcium cuprate complexes of unique and different chemical reactivity. The organocalcium cuprate complexes are composed of a mixture or combination of an aliphatic, aryl, heterocyclic, arylalkyl or polymeric calcium cuprate and alkali metal salts. The alkali metal salts are from the copper(I) salt, which is preferably a thienyl cyanide, cyanide, or halide. More preferably, it is a thienyl cyanide or a cyanide.

The copper(I) salts that are reactive with the organocalcium reagents of the present invention are preferably soluble copper(I) salts in an ethereal, polyethereal, or hydrocarbon solvent. They include, but are not limited to, CuCN.2LiBr, CuI, CuBr, CuCl, CuF, lithium thienylcyanocuprate, or other Cu(I) salts with nonprotic anions. Preferably, the Cu(I) salt is CuCN.2LiBr or lithium thienylcyanocuprate.

The reaction conditions used for the formation of the organocalcium cuprate reagents are those typically designed to preserve the integrity of the organocalcium cuprate reagents. These conditions include the exclusion of water and oxygen, temperatures of less than about 100° C., preferably between about −140° C. and about 100° C., and more preferably between about −80° C. and about 30° C. The copper is usually added in an equimolar amount relative to the organocalcium reagent, but can be added in an excess amount. The formation of the calcium cuprate reagents is typically carried out in the same medium used to produce the organocalcium reagent.

Reaction of the organocalcium reagent prepared from an organic halide and the highly reactive calcium, with acid chlorides in the absence of a Cu(I) salt, typically afford complex mixtures of products. However, in the presence of a Cu(I) salt, high yields, i.e., greater than about 50% and often greater than about 70%, of ketone formation are observed. Example 3 and Table II presents some specific examples of the ketone formation reactions of the calcium cuprates with benzoyl chloride.

The reaction conditions for the ketone formation reactions include temperatures of less than about 100° C., preferably between about −140° C. and about 100° C., more preferably between about −80° C. and about 30° C., and the absence of oxygen or protic solvents.

These calcium cuprate compounds also undergo the conjugate 1,4-addition reactions with $\alpha,\beta$-unsaturated species. Example 4 and Table III presents some specific examples of conjugate 1,4-addition reactions with $\alpha,\beta$-unsaturated ketones, utilizing these calcium cuprates.

The $\alpha,\beta$-unsaturated species that undergo the 1,4-addition reactions can be any of a variety $\alpha,\beta$-unsaturated species. For example, they can be $\alpha,\beta$-unsaturated ketones, aldehydes, esters, and amides. They can be acyclic, aryl, and even sterically hindered. If they are sterically hindered, i.e., if any group in the molecule hinders attack of the $\beta$-position, it is preferred that the reaction mixture contains $BF_3$ etherate and chlorotrimethylsilane, (TMSCl). These reagents perform the function of activation of the $\alpha,\beta$-unsaturated system. Other useful reagents such as this include alkyl and phosphines.

Typically, the product yields of the 1,4-addition reactions using the organocalcium cuprate reagents are greater than about 40%, and preferably greater than about 70%. The reaction conditions for the 1,4-addition reactions include temperatures of less than about 100° C., preferably between about −140° C. and about 100° C., more preferably between about −80° C. and about 30° C., and the absence of oxygen.

Preparation and Reactions of Calcium Metallocycle

Calcium complexes of 1,3-dienes can be prepared by reaction of the highly reactive calcium with a wide variety of conjugated dienes, e.g., 1,3-dienes, such as 1,4-diphenyl-1,3-butadiene, 1,3-butadiene, 2,3-dimethyl-1,3-butadiene, 2-methyl-1,3-butadiene, or any mono-, di-, tri-, or tetra-substituted 1,3-diene to form 2-butene-1,4-diylcalcium reagents. The dienes can be symmetrical or unsymmetrical. They can be open-chain hydrocarbons containing at least two conjugated double bonds or cyclic hydrocarbons containing at least two conjugated exocyclic double bonds, such as occur in 1,2-dimethylenecyclohexane, 1,2-dimethylenecyclopentane, and 1,2-dimethylenecycloheptane, for example. Preferably, the 1,3-dienes do not contain any functional groups that react with the active calcium preferentially to the 1,3-diene functionality. The resulting bisorganocalcium reagents readily undergo alkylation reactions with a variety of electrophiles, i.e., compounds that are deficient in electrons, in a highly regio- and stereospecific manner (Table IV).

The electrophiles include, but are not limited to, organodihalides, such as 1,3-dibromopropane, 1,4-dibromobutane, $\alpha,\omega$-alkylene dihalides, mono- and dihalosilanes, mono- and dihalostannanes, acid chlorides, esters, amides, nitriles, gemdihalides, $\alpha,\omega$-alkyl halonitriles, and the like. The reactions with the electrophiles, such as the organodihalides, typically yield 4-, 5-, and 6-membered rings in yields greater than about 50%, and often greater than about 70% isolated yield. Preferably, and advantageously, the stereochemistry of these reactions is stereospecific.

This chemistry can also be extended to 2,3-dimethyl-1,3-butadiene, which is a molecule which is much more difficult to reduce. Reaction of the resulting calcium complex with 1,3-dichloropropane and 1,4-dibromobutane produces the 5-membered ring product and 6-membered ring products in greater than about 50% yield. Further reactions of 2-butene-1,4-diyl calcium species to produce spirocycles, lactones, lactams, and vicinal diols are described below.

The reaction conditions for production of calcium reagents with 1,3-dienes include temperatures of less than about 100° C., preferably between about −140° C. and about 100° C., and more preferably between about −80° C. and about 100° C. and the absence of oxygen. The subsequent reactions of these 2-butene-1,4-diylcalcium complexes include temperatures of less than about 100° C., preferably between about −140° C. and about 100° C., and more preferably between about −80° C. and about 100° C., and the absence of oxygen.

Preparation of Polymers From Soluble Highly Reactive Calcium

Significantly, the soluble highly reactive calcium species of the present invention reacts with organic halides substituted with more than one halide atom, such as dihalothiophenes and dihalobenzenes. Upon reaction with organodihalides, mono- or diorganocalcium compounds typically form which are capable of being converted into a wide variety of polymeric compounds.

It is also envisioned that the soluble highly reactive calcium species of the present invention will react with other dihaloarenes, such as 2,5-dichlorothiophene, 2,7-dibromo-9-fluorenone, 2,7-dibromofluorene, 2,5-dibromopyridine, 3,4-dibromothiophene, 4,4'-dibromobiphenyl, and 9,10-dibromoanthracene, $Br-C_6H_4-CH_2Br$, $Br-C_6H_4-CH_2-C_6H_4-Br$, and the like. Each of these organodihalides can optionally be functionalized with groups such as —CN, —CO$_2$CH$_2$CH$_3$, —OH. The dihaloarenes can also include heterocyclic arenes.

Preferably, the soluble highly reactive calcium species of the present invention reacts with dihalothiophene and dihalobenzene. As a specific example, it can react with 2,5-dibromothiophene and 1,4-dibromobenzene.

Furthermore, it is envisioned that the highly reactive calcium species of the present invention will react with trihaloarenes, such as 1,3,5-tribromobenzene, and the like.

The mono- and/or disubstituted organocalcium species formed can further react with electrophiles, such as those disclosed above, as well as numerous others, as for example terephthaloyl chloride, to form unique polymeric materials. Preferably, the resultant polymers formed are two-dimensional linear polymers. However, both the monosubstituted and disubstituted organocalcium species formed should be capable of generating novel block polymers.

Typically, the formation of the polymers includes the use of a catalyst, such as NiCl$_2$ and low temperatures. These polymeric materials, especially two-dimensional linear polymers, have significant applicability in nonlinear optical materials, highly conductive materials, magnetic storage devices, etc.

The soluble highly reactive calcium of the present invention will also likely react with derivatives of C$_{60}$ and C$_{70}$ fullerenes. Both mono- and disubstituted calcium fullerenes are envisioned. These calcium derivatives will then cross couple with most, if not all, of the electrophiles discussed above. Furthermore, these calcium derivatives could be used to incorporate fullerenes into polymers and generate novel block copolymers. Examples would include copolymers of 2,5-thienylene/fullerene, phenylene/fullerene, and acetylene/fullerene.

Thus, the use of the highly reactive calcium species of the present invention should allow for the preparation of a wide variety of substituted fullerenes. These substituted fullerenes are envisioned to be of significant importance in biological applications, as nonlinear optical materials, highly conductive materials, magnetic storage devices, etc.

Spiroannelation

Highly reactive calcium reacts smoothly with cyclic hydrocarbons containing at least two conjugated exocyclic double bonds to produce the corresponding 2-butene-1,4-diylcalcium complexes in high yield. The cyclic hydrocarbons can be any of a variety of cyclic alkanes or cyclic alkenes containing at least two conjugated exocyclic double bonds providing, however, that any double bonds in the ring are not in conjugation with the exocyclic double bonds. Preferably, these cyclic hydrocarbons do not contain any additional functional groups that react with the highly reactive calcium preferentially to the conjugated exocyclic double bond functionalities. More preferably, the cyclic hydrocarbons are cycloalkanes containing at least two exocyclic double bonds. Most preferably, the cycloalkanes are 1,2-dimethylenecycloalkanes, such as 1,2-dimethylenecyclohexane, 1,2-dimethylenecyclopentane, and 1,2-dimethylenecycloheptane. These resulting 2-butene-1,4-diylcalcium complexes prepared from cyclic hydrocarbons with conjugated exocyclic double bonds react with a variety of electrophiles, i.e., compounds that are deficient in electrons, to form carbocycles, including spirocycles, i.e., structures with two rings having one carbon atom in common. Spirocycles, particularly the spiro[4.5]decane and spiro[5.5]undecane ring systems, constitute the basic carbon framework found in a wide variety of naturally occurring sesquiterpenes.

The electrophiles include, but are not limited to, organodihalides, such as 1,2-dibromoethane, 1,3-dibromopropane, 1,4-dibromobutane, and 1,5-dibromopentane, organoditosylates, such as ethylene glycol di-p-tosylate, haloalkylnitriles, such as Br(CH$_2$)$_n$CN compounds wherein n=1–3, organoditriflates, esters, amides, and the like. The reactions with the electrophiles typically yield carbocycles in isolated yields greater than about 40%, and often greater than about 50%.

Significantly, a wide variety of ring sizes can be generated using this approach, making this an advantageous method for the easy preparation of a wide variety of carbocycles, particularly spirocycles. Furthermore, the spirocycles typically formed by this method contain functional groups, such as an exocyclic double bond or a keto group, in one of the rings that can be used for further elaboration of these molecules.

The reaction conditions for production of 2-butene-1,4-diylcalcium complexes resulting from the reaction of highly reactive calcium with cyclic hydrocarbons having conjugated exocyclic double bonds include ambient or room temperatures, i.e., about 20° C. to 30° C., the absence of oxygen, and an excess of highly reactive calcium. Generally, these conditions include use of ethereal, polyethereal, or hydrocarbon solvents. Preferably, the reactions are carried out under an inert atmosphere of argon or nitrogen with a ratio of calcium to cyclic hydrocarbon present in a range of about 1:1 to 2:1 molar equivalents. The reaction time is preferably 3–4 hours, and the solvent is preferably an ether or polyether solvent such as diethyl ether, dimethyl ether, tetrahydrofuran, and the like. More preferably, the solvent is tetrahydrofuran.

The subsequent reactions of these 2-butene-1,4-diylcalcium complexes with electrophiles to produce carbocycles, particularly spirocycles, include temperatures of less than about 100° C., preferably at a temperature of about −80° C. to about 80° C., and the absence of oxygen. Generally, these reactions are carried out in ethereal, polyethereal, or hydrocarbon solvents. Preferably, the reactions are carried out in tetrahydrofuran under an inert atmosphere of argon or nitrogen at a temperature of about −78° C. with subsequent warming. The method for the preparation of keto-functionalized products also include a step whereby H$_3$O$^+$ is added subsequent to warming.

Preparation of γ-Lactones Including Spiro γ-Lactones

A useful application of substituted 2-butene-1,4-diylcalcium complexes formed from a conjugated diene, e.g., either cyclic hydrocarbons containing at least two conjugated exocyclic double bonds or open-chain hydrocarbons containing at least two conjugated double bonds, is the novel one-pot synthesis of γ-lactones, preferably spiro γ-lactones. The cyclic hydrocarbons useful in this synthetic method are the same as those discussed above with respect to spiroannelation. The open-chain conjugated dienes can be a variety of dienes containing at least two double bonds in conjugation, i.e., separated by a carbon-carbon single bond. Preferably, these open-chain conjugated dienes do not contain any additional functional groups that react with the highly reactive calcium preferentially to the conjugated double bond functionalities. More preferably, the open chain conjugated dienes are 1,3-dienes. Most preferably the open chain conjugated dienes are 1,3-butadienes, such as 2,3-dimethyl-1,3-butadiene.

Spiro γ-lactones and other γ-lactones can be obtained in yields in excess of 50%, preferably in excess of 60%, by initially treating 2-butene-1,4-diylcalcium complexes, with a ketone or aldehyde to give the corresponding 1,2-addition adduct. Preferably, this reaction is carried out at a temperature of about −90° C. to about −70° C. The ketone or aldehyde is preferably present in an amount of approximately one mole of ketone or aldehyde per mole of 2-butene-1,4-diylcalcium complex. The ketones can be any alkyl, aryl, or mixed alkyl-aryl ketone. Preferably, the ketone is selected from the group consisting of acetone, cyclohexanone, and cyclopentanone. The aldehydes can be any alkyl or aryl aldehyde. Preferably, the aldehyde is selected from the group consisting of benzaldehyde and acetaldehyde. It is noted that the aryl ketones and aryl aldehydes include within their scope groups containing heteroatoms such as nitrogen, for example.

Subsequent to this initial step, carbon dioxide is combined with the 1,2-addition adduct to form a nucleophilic addition product. This reaction is preferably carried out by bubbling gaseous carbon dioxide through the reaction mixture containing the 1,2-addition adduct. This nucleophilic addition product is a calcium salt of an organic molecule containing both an alkoxy (—CR$_2$O—) and a carboxylate group (—COO−). The nucleophilic addition reaction with CO$_2$ preferably occurs at a temperature of about 0° C. to about 20°-30° C., preferably about 25° C. Acidic hydrolysis using an aqueous acid, followed by a slight warming of the reaction mixture to a temperature of about 30° C. to about 50° C. forms the γ-lactone. The aqueous acid is preferably a relatively strong mineral, i.e., inorganic, acid. More preferably, the acid is selected from the group consisting of HCl, H$_2$SO$_4$, and H$_3$PO$_4$. Most preferably, the acid is HCl. Significantly, this approach can also be used to prepare spiro γ-lactones containing two spiro centers.

The following scheme illustrates this route for spiro γ-lactone synthesis.

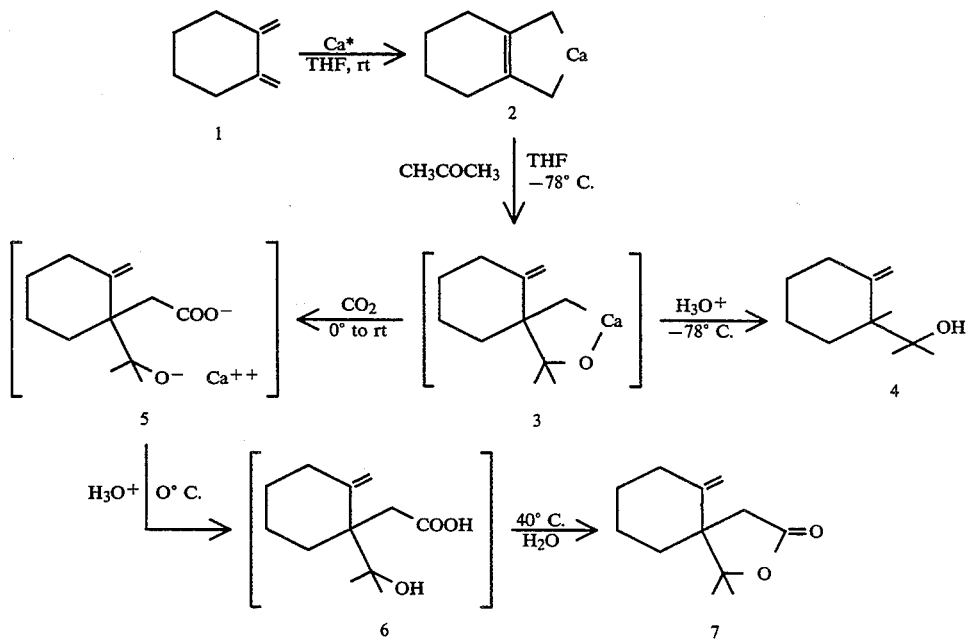

Referring to the above scheme, treatment of 1,2-dimethylenecyclohexanecalcium (2) with one molar equivalent of acetone at −78° C. results in the formation of a 1,2-addition adduct (3) derived from the incorporation of one molecule of acetone with the diene complex. (The actual structure of this complex is unknown.) Protonation of the 1,2-addition adduct (3) at −78° C. yields a tertiary alcohol containing a quaternary center (4). Carbon dioxide is bubbled as a second electrophile through the reaction mixture at 0° C. to room temperature (about 20°-30° C., preferably about 25° C.). Intermediate (3) reacts with carbon dioxide, yielding presumably a calcium salt of an organic molecule containing both an alkoxy and a carboxylate group (5). After acidic hydrolysis followed by slight warming, a spiro γ-lactone, 4,4-dimethyl-6-methylene-3-oxaspir[4.5]decan-2-one (7) is obtained. Treatment of (2) with two molar equivalents of acetone at −78° C. followed by acidic hydrolysis at −78° C. also yields (4), indicating that the initially formed adduct (3) does not undergo further addition with unreacted acetone under the reaction conditions. Thus, both acetone and subsequently added $CO_2$ are delivered to the original diene at desired positions.

Significantly, this approach can also be used to prepare spiro γ-lactones containing two spiro centers. For example, (2) can be treated with cyclopentanone at −78° C. and the reaction mixture then bubbled with $CO_2$. Workup gives 11-methylene-14-oxadispiro[4.0.5.3]tetradecan-13-one. Similar chemistry can be observed when cyclohexanone is used as the first electrophile.

A notable advantage of this new γ-lactone synthesis is that the construction of a quaternary center and the introduction of both a hydroxyl and a carboxyl used for lactonization are accomplished in one synthetic operation. Remarkably, this chemistry can be easily extended to the calcium complex of acyclic 1,3-diene. The following scheme gives an outline for the synthesis of spiro γ-lactones from (2,3-dimethyl-2-butene-1,4-diyl)calcium (11). Generally, reaction of a cyclic ketone with (11) at −78° C. results in initial attack at the 2-position of the diene complex, giving an internal alkoxy Grignard (12). After warming up, the intermediate is allowed to react with carbon dioxide at 0° C. to room temperature. Upon hydrolysis and gentle heating, a spiro γ-lactone containing a quaternary center is obtained (14). The method is equally useful for the preparation of γ-lactones. Use of an acyclic ketone or aldehyde instead of a cyclic ketone will result in the synthesis of the corresponding γ-lactone.

10

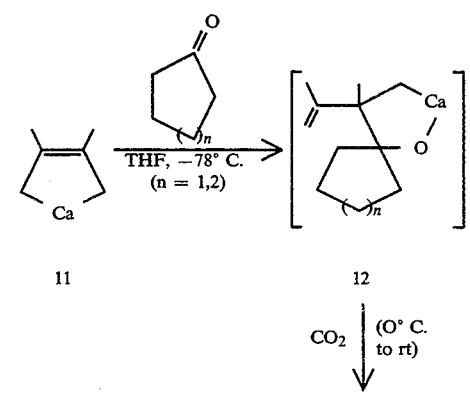

11  12

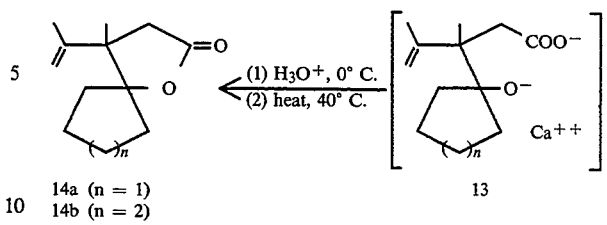

14a (n = 1)
14b (n = 2)

13

Preparation of δ-Lactones Including Spiro δ-Lactones

A direct, one-pot process for the synthesis of spiro δ-lactones, δ-lactones, and alcohols utilizing active calcium is also provided. This technique involves the treatment of a conjugated diene-calcium reagent, i.e., a 2-butene-1,4-diylcalcium complex, with an epoxide affording an intermediary organocalcium addition complex, i.e., a 1,2-addition adduct, derived from the incorporation of one molecule of epoxide with the diene-calcium complex. Upon warming, the intermediate undergoes further nucleophilic addition to carbon dioxide. After acidic hydrolysis and subsequent warming, a δ-lactone is afforded by the lactonization of the resulting δ-hydroxy acid.

Spiro δ-lactones and other δ-lactones can be obtained in yields in excess of 50%, preferably in excess of 60%, by initially treating 2-butene-1,4-diylcalcium complexes, with an epoxide to give the corresponding addition adduct. Preferably, this reaction is carried out at a temperature of about −90° C. to about −70° C. The epoxide is preferably present in an amount of approximately one mole of epoxide per mole of 2-butene-1,4-diylcalcium complex. The epoxide can have alkyl, aryl, or heterocyclic substituents about the epoxide group. Suitable epoxides include, but are not limited to, ethylene oxide, propylene oxide, t-butylene oxide, cyclohexene oxide and styrene oxide. Preferably, the epoxide is selected from the group consisting of ethylene oxide, propylene oxide, 1-butylene oxide, and cyclohexene oxide.

Subsequent to this initial step, carbon dioxide is combined with the addition adduct to form a nucleophilic addition product. This reaction is preferably carried out by bubbling gaseous carbon dioxide through the reaction mixture containing the addition adduct. This nucleophilic addition product is a calcium salt of an organic molecule containing both an alkoxy and a carboxylate group (—COO−). The nucleophilic addition reaction with $CO_2$ preferably occurs at a temperature of about 0° C. to about 20°–30° C., preferably about 25° C. Acidic hydrolysis using an aqueous acid, followed by a slight warming of the reaction mixture to a temperature of about 30° C. to about 50° C. forms the δ-lactone. The aqueous acid is preferably a strong mineral, i.e., inorganic, acid. More preferably, the acid is selected from the group consisting of HCl, $H_2SO_4$, and $H_3PO_4$. Most preferably, the acid is HCl. Significantly, this approach can also be used to prepare spiro δ-lactones containing two spiro centers.

The following scheme illustrates the general reaction scheme.

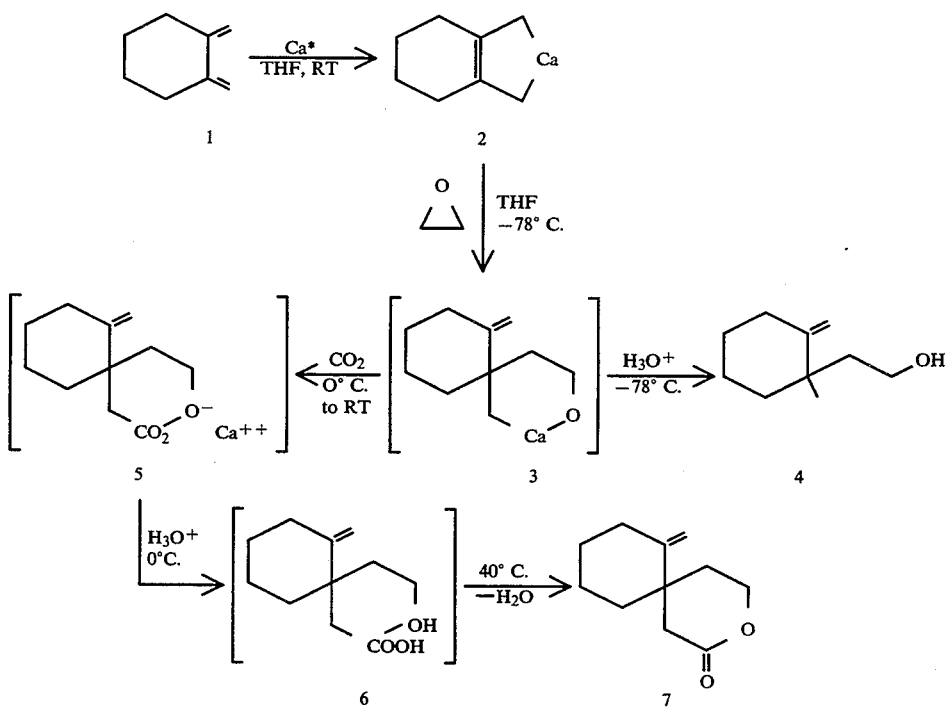

The above Scheme illustrates a route for spiro δ-lactone synthesis from the calcium complex of 1,2-bis(methylene)cyclohexane (1). Initially, treatment of 1,2-bis(methylene)cyclohexane calcium reagent (2), i.e., a 2-butene-1,4-diylcalcium complex, with an excess of ethylene oxide at −78° C., results in the formation of the 1,2-addition adduct (3) derived from the incorporation of one molecule of epoxide with the diene complex. Significantly, the bis-organocalcium reagent (2) reacts with only one mole of epoxide, and preferably reacts with 100% regioselectivity in the 2-position, to give the addition adduct (3). Protonation of this adduct (3) at −78° C. affords a primary alcohol containing a quaternary center (4). Upon warming, 3 reacts with $CO_2$ to yield the calcium salt of a δ-hydroxy acid (5). Upon acidic hydrolysis, the δ-hydroxy acid (6) is formed which upon slight warming undergoes lactonization to yield the spiro δ-lactone (7). It is significant to note that even though (2) is treated with an excess of the epoxide, only one equivalent of the epoxide reacts with (2). Importantly, this approach can be used to prepare bicyclic spiro δ-lactones. For example, 1,2-bis(methylene)cyclohexane-calcium reagent (2) can be treated with cyclohexene oxide at −78° C. and the reaction mixture bubbled with $CO_2$ at 0° C. with warming to room temperature.

This approach is also equally applicable to acyclic 1,3-dienes and provides a facile route to δ-lactones. The following scheme displays an outline for the synthesis of δ-lactones from (2,3-dimethyl-2-butene-1,4-diyl)calcium (9). Reaction of cyclohexene oxide with (9) at −78° C. results in an initial attack at the 2-position of the calcium-diene complex, affording an internal alkoxy calcium complex (10). After gradual warming to 0° C., intermediate (10) is reacted with carbon dioxide to presumably yield the calcium salt (11), which contains both an alkoxy and a carboxylate functional group. Upon hydrolysis, the δ-hydroxy carboxylic acid is presumably formed and gently heated to afford a bicyclic δ-lactone (12), as a mixture of diastereomers, accommodating a quaternary center.

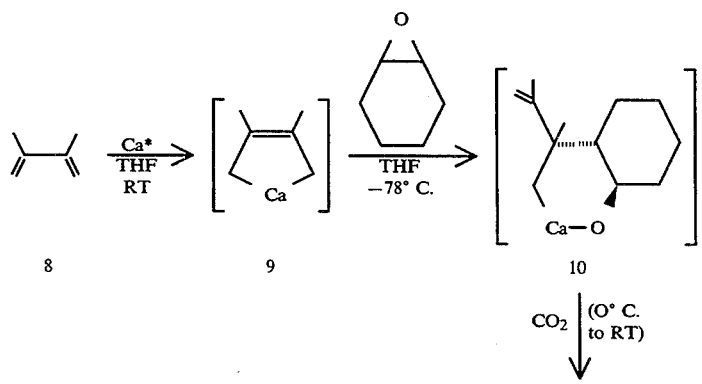

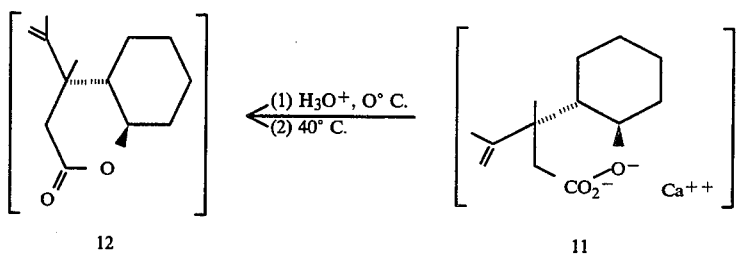

This methodology exhibits relatively good regioselectivity when unsymmetric epoxides are utilized as the primary electrophile. The attack of the unsymmetric epoxide occurs at the less sterically hindered carbon. Hydrolysis after treatment with 2-epoxybutane and 1,2-epoxyhexane, respectively, affords the secondary alcohols with a quaternary carbon center.

The overall procedure of the spiro δ-lactone and δ-lactone syntheses can be thought of as a molecular assembling process in which three simple independent species, i.e., a conjugated diene, an epoxide, and carbon dioxide, mediated by active calcium are used to build a complex organic molecule in a well-controlled fashion. In the process, the construction of a quaternary carbon center and the introduction of both a hydroxyl group and a carboxyl group required for lactonization are achieved in one synthetic operation.

Preparation of γ-Lactams from Conjugated Diene-Calcium Reagents

The present invention also provides a molecular assembling process in which three simple independent species, i.e., a conjugated diene, an imine, and carbon dioxide, mediated by active calcium are utilized to construct a γ-lactam in an orderly fashion. See the following reaction scheme. Also, the construction of a quaternary carbon center is generated in the process.

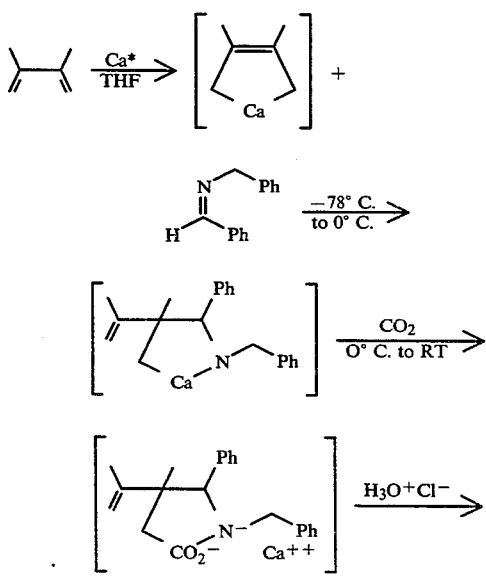

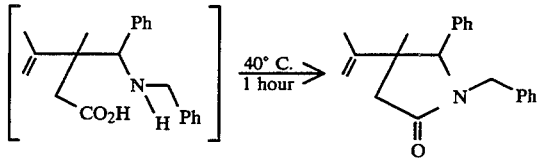

γ-Lactams can be obtained in yields in excess of 40%, preferably in excess of 60%, by initially treating 2-butene-1,4-diylcalcium complexes, with an imine to give the corresponding 1,2-addition adduct. Preferably, this reaction is carried out at a temperature of about −90° C. to about −70° C. and subsequently allowed to warm to about 0° C. The imine is preferably present in an amount of approximately one mole of imine per mole of 2-butene-1,4-diylcalcium complex. This reaction is very general and will work with any imine according to the following formula:

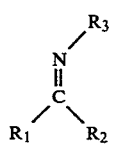

$R_1$, $R_2$, or $R_3$ = alkyl, aryl, vinyl, heterocycle

Examples of suitable imines include, but are not limited to, N-benzylideneaniline, benzophenone imine, acetone imine, N-benzylidenemethylamine, and acetophenone imine.

Subsequent to this initial step, carbon dioxide is combined with the 1,2-addition adduct to form a nucleophilic addition product. This reaction is preferably carried out by bubbling gaseous carbon dioxide through the reaction mixture containing the 1,2-addition adduct. This nucleophilic addition product is a calcium salt of an organic molecule containing both an amine anion and a carboxylate group (—COO−). The nucleophilic addition reaction with $CO_2$ preferably occurs at a temperature of about 0° C. to about 20°–30° C., preferably about 25° C. Acidic hydrolysis using an aqueous acid, followed by a slight warming of the reaction mixture to a temperature of about 30° C. to about 50° C. forms the γ-lactam. The aqueous acid is preferably a strong mineral, i.e., inorganic, acid. More preferably, the acid is selected from the group consisting of HCl, $H_2SO_4$, and $H_3PO_4$. Most preferably, the acid is HCl.

Preparation of Chiral Vicinal Diols

The incorporation of an unsymmetric, chiral epoxide containing a hydroxyl functional group as a primary electrophile, followed by treatment with a proton source, affords a vicinal diol containing a chiral quaternary carbon center. See the following reaction scheme. It is significant to note that the 1,3-diene calcium complex tolerates the presence of an unprotected hydroxyl group in this transformation.

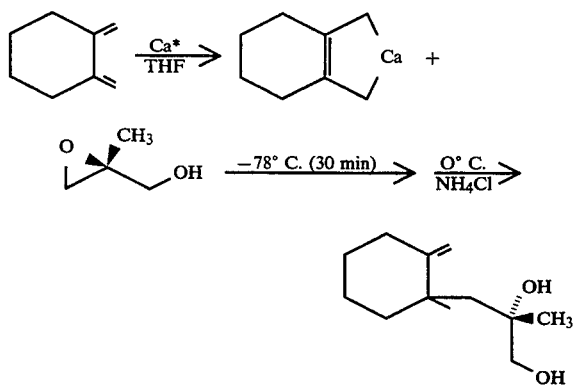

Vicinal diols can be obtained in yields in excess of 40%, preferably in excess of 60%, by initially treating 2-butene-1,4-diylcalcium complexes, with an unsymmetrical chiral epoxide to give the corresponding epoxide ring opened addition adduct. Preferably, this reaction is carried out at a temperature of about −90° C. to about −70° C. The chiral epoxide is preferably present in an amount of approximately one mole of epoxide per mole of 2-butene-1,4-diylcalcium complex. This reaction is very general and will work with any chiral α-hydroxy epoxide of the following formula:

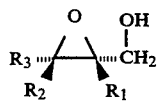

wherein $R_1$ and $R_2$ and $R_3$ can be alkyl, aryl, vinyl, or heterocyclic groups. Examples of suitable chiral epoxides include, but are not limited to, R- or S- 3-hydroxy-2-methyl-1-propene oxide, R- or S- 3-hydroxy-1-methyl-1-propene oxide, R- or S- 3-hydroxy-2-ethyl-1-propene oxide, and R- or S- 3-hydroxy-2-phenyl-1-propene oxide.

Subsequent to this initial step, acidic hydrolysis using an aqueous acid, followed by a slight warming of the reaction mixture to a temperature of about 30° C. to about 0° C. forms the vicinal diol. The aqueous acid is preferably a relatively strong mineral, i.e., inorganic, acid. More preferably, the acid is selected from the group consisting of $NH_4Cl$, $HCl$, $H_2SO_4$, and $H_3PO_4$. Most preferably, the acid is $NH_4Cl$.

The invention will be further exemplified with respect to the various specific and preferred embodiments and techniques. It should be understood, however, that many variations and modifications may be made while remaining within the scope of the invention.

Experimental Examples

Melting points were determined on a Thomas-Hoover melting point apparatus or on an Electrothermal TM melting point apparatus and are corrected. IR spectra were taken on an Analect TM RFX-30 Fourier Transform Infrared (FTIR) spectrometer. The spectra were taken of neat samples between NaCl or KBr plates or as KBr pressed pellets. $^1H$ NMR spectra were recorded on a Nicolet TM NT-360 (360 MHz) or on a Varian TM VXR-200 (200 MHz) spectrometer. All chemical shifts are reported in parts per million (δ) downfield from internal tetramethylsilane. Fully decoupled $^{13}C$ NMR spectra and Distortionless Enhanced Polarization Transfer (DEPT) experiments were recorded on a Varian TM VXR-200 (50 MHz) spectrometer. The center peak of $CDCl_3$ (77.0 ppm) was used as the internal reference. Two-dimensional Correlation Spectroscopy (COSY) spectra were recorded on a Nicolet TM NT-360 (360 MHz) spectrometer. High resolution mass spectra were performed by the Midwest Center for Mass Spectrometry at the University of Nebraska-Lincoln using a Kratos TM MS-80 mass spectrometer. Elemental analyses were performed by Oneida Research Services, Inc., Whitesboro, N.Y. Gas chromatography analysis was done on a Hewlett-Packard TM 5890A chromatograph using stainless steel columns (12 ft × ⅛ in) packed with OV-17 (3%) on 100/120 Chromosorb TM G-AW or SE-30 (5%) on 100/120 Chromosorb TM G-NAW (both of which are available from Supelco, Inc., Bellefonte, Pa.). Analytical thin-layer chromatography was performed using Merck TM 5735 (0.2 mm thickness) indicating plates (available from Whatman Ltd., Maidstone, Kent, England). Preparative thin-layer separations were performed using Anatech TM silica gel GF (1 or 2 mm thickness) preparative plates (available from Newark, Del.), or using Whatman TM PLKC 18F linear-K reversed phase (1 mm thickness) preparative plates (available from Whatman Ltd., Maidstone, Kent, England). Low-temperature reactions were performed utilizing a Neslab Endocal TM ULT-80 refrigerated circulating bath or utilizing dry ice/acetone baths. All manipulations were carried out on a dual manifold vacuum/argon system. The Linde TM prepurified grade argon was further purified by passing it through a 150° C. catalyst column (BASF TM R3-11), a phosphorous pentoxide column, and a column of granular potassium hydroxide. Lithium and naphthalene, byphenyl, or anthracene were weighed out and charged into reaction flasks under argon in a Vacuum Atmospheres Company dry box. Tetrahydrofuran was freshly distilled under argon from sodium/potassium alloy. Anhydrous calcium(II) iodide and calcium(II) bromide were purchased from Cerac, Inc., Milwaukee, Wis. Anhydrous calcium(II) chloride was purchased from Alfa Chemicals, Denver, Colo. 2,3-Dimethyl-1,3-butadiene was distilled prior to use. Other commercially available reagents were used as received unless specially noted.

EXAMPLE 1

Typical Procedure for Preparation of Highly Reactive Calcium

Lithium (9.0 mmol) and biphenyl (9.8 mmol) were stirred in freshly distilled THF (20 mL) under argon until the lithium was substantially completely consumed (approximately 2 hours). To a well-suspended solution of $CaI_2$ or $CaBr_2$ in freshly distilled THF (20 mL), the preformed lithium biphenylide was transferred via a cannula at room temperature. Typically, an approximate equivalent ratio of the calcium salt to the lithium biphenylide was used; i.e., 1 mole of the Ca(II) salt to 2 moles of the lithium biphenylide; however, when the resultant soluble highly reactive calcium was used in further reactions, an excess (1.5–2.0 equivalents) of the calcium salt was used in the preparation of the soluble highly reactive calcium. The reaction mixture was stirred for 1 hour at room temperature prior to use.

EXAMPLE 2

Formation of Organocalcium Reagents and Use in a Grignard-Type Reactions

The following experimental procedure is representative of the reactions set forth below in Table I. Highly reactive calcium (3.07 mmol), prepared from lithium biphenylide (6.15 mmol) and excess $CaI_2$ (4.91 mmol) in THF (30 mL), was cooled to $-78°$ C. The color turned green upon cooling. An organocalcium reagent was prepared by adding p-chlorotoluene (324 mg, 2.56 mmol) to this mixture via a disposable syringe at $-78°$ C. The reaction mixture was allowed to warm to $-20°$ C. It was stirred at $-20°$ C. for 30 minutes. The reaction mixture was then cooled to $-35°$ C. A Grignard-type reaction was carried out by adding excess cyclohexanone (510 mg, 5.20 mmol) to the solution of the organocalcium reagent via a disposable syringe at $-35°$ C. The resulting mixture was gradually warmed to room temperature and was stirred at room temperature for 30 minutes. The reaction mixture was again cooled to $-35°$ C. Neutral $H_2O$ (distilled water, 20 mL) was added at $-35°$ C. After being warmed to room temperature, the reaction mixture was filtered through a small pad of Celite TM filter agent (available from Aldrich Chemical Co., Milwaukee, Wis.) and was washed with $Et_2O$ (50 mL). The aqueous layer was extracted with $Et_2O$ ($3 \times 30$ mL). The combined organic phases were washed with $H_2O$ (15 mL), and dried over anhydrous $MgSO_4$. Removal of solvent and flash-column chromatography on silica gel (100 g, 230–400 mesh, available from EM Science; Gibbstown, N.J.) afforded 1-(p-methylphenyl)cyclohexanol (417 mg, 86% yield) as white crystals: mp 53°–55° C.; IR (KBr) 3419, 3030, 2935, 2843, 1514, 1446, 1392, 1134, 1036, 964, 810 cm$^{-1}$; $^1H$ NMR (200 MHz, $CDCl_3$) δ 7.35–7.45 (m, 2 H), 7.10–7.20 (m, 2 H), 2.33 (s, 3 H), 1.55–1.85 (m, 11 H); $^{13}C$ NMR (50 MHz, $CDCl_3$) δ 146.5, 136.2, 128.9, 124.5, 72.9, 38.9, 25.5, 22.2, 20.9. Known compound: IR, see Sadtler 36367; $^1H$-NMR, see Sadtler 21529; $^{13}C$-NMR, see Sadtler 5269.

As shown in Table I, 1-bromooctane and 1-bromo-3-phenoxypropane reacted with the calcium species at $-78°$ C. to form the corresponding alkylbromocalcium reagents, which underwent Grignard-type reactions with cyclohexanone to produce the tertiary alcohols in 79% and 75% yields, respectively. Oxidative addition of alkyl chlorides to this soluble calcium species was also very efficient at low temperature ($-78°$ C.). 1-Chlorooctane gave 1-octylcyclohexanol in 83% yield. Similar results were noted for the secondary halides. Bromocyclohexane reacted readily with the calcium species at $-78°$ C. and the resulting organocalcium reagent underwent carbonyl addition to give the alcohol in 75% yield.

Significantly, the highly reactive calcium species reacted rapidly with tertiary bromides at $-78°$ C. For example, the Grignard-type reaction for 1-bromoadamantane utilizing the reactive calcium afforded 1-(1-adamantyl)cyclohexanol in 80% yield. The direct reaction of 1-bromoadamantane with metals is well known to yield mainly reductive cleavage or dimerization. Accordingly, this method represents a significant new approach to the 1 -metalloadamantane.

Reactions of aryl halides with reactive calcium required slightly higher temperatures, up to $-30°$ C. for aryl bromides and up to $-20°$ C. for aryl chlorides. The aryl calcium compounds are very stable at room temperature. Reactions of m-bromotoluene, m-bromoanisole, and p-chlorotoluene with the soluble highly reactive calcium complex gave the corresponding arylcalcium reagents in quantitative yields based on the GC analyses of reaction quenches. The 1,2-addition of these arylcalcium compounds with ketones gave the alcohols in excellent yields (76%, 79% and 86%, respectively). The soluble highly reactive calcium readily reacted with fluorobenzene at room temperature to form the corresponding organometallic compound which underwent an addition reaction with cyclohexanone to give 1-phenylcyclohexanol in 85% yield.

1-Octylcyclohexanol (83% yield): IR (neat) 3379, 2929, 2856, 1448, 1259, 968 cm$^{-1}$; $^1H$ NMR (200 MHz, $CDCl_3$) δ 1.15–1.65 (m, 25 H), 0.88 (t, J=7.0 Hz, 3 H); $^{13}C$ NMR (50 MHz, $CDCl_3$) δ 71.4, 42.5, 37.5, 31.9,

TABLE I

| | Grignard-Type Reactions of Organocalcium Reagents with Cyclohexanone | | | |
|---|---|---|---|---|
| Entry | Halide | $CaX_2$ | Product[a] | % Yield[b] |
| 1 | $Cl(CH_2)_7CH_3$ | $CaI_2$ | $1\text{-}(CH_2)_7CH_3\text{-}1\text{-}OH\text{-}c\text{-}C_6H_{10}$ | 83 |
| 2 | $Br(CH_2)_7CH_3$ | $CaI_2$ | $1\text{-}(CH_2)_7CH_3\text{-}1\text{-}OH\text{-}c\text{-}C_6H_{10}$ | 79 |
| 3 | $Br(CH_2)_3OPh$ | $CaBr_2$ | $1\text{-}(CH_2)_3OPh\text{-}1\text{-}OH\text{-}c\text{-}C_6H_{10}$ | 75 |
| 4 | $Br\text{-}c\text{-}C_6H_{11}$ | $CaBr_2$ | $1\text{-}c\text{-}C_6H_{11}\text{-}1\text{-}OH\text{-}c\text{-}C_6H_{10}$ | 75 |
| 5 | Br-adamantyl | $CaBr_2$ | 1-adamantyl-cyclohexanol | 80 |
| 6 | $BrC_6H_4(m\text{-}CH_3)$ | $CaI_2$ | $1\text{-}C_6H_4(m\text{-}CH_3)\text{-}1\text{-}OH\text{-}c\text{-}C_6H_{10}$ | 76 |
| 7 | $ClC_6H_4(p\text{-}CH_3)$ | $CaI_2$ | $1\text{-}C_6H_4(p\text{-}CH_3)\text{-}1\text{-}OH\text{-}c\text{-}C_6H_{10}$ | 86 |
| 8 | FPh | $CaI_2$ | $1\text{-}Ph\text{-}1\text{-}OH\text{-}c\text{-}C_6H_{10}$ | 85 |
| 9 | $BrC_6H_4(m\text{-}OCH_3)$ | $CaBr_2$ | $1\text{-}C_6H_4(m\text{-}OCH_3)\text{-}1\text{-}OH\text{-}c\text{-}C_6H_{10}$ | 79 |

[a]All new substances have satisfactory spectroscopic data including IR, $^1H$ NMR, $^{13}C$ NMR, and high-resolution mass spectral data, as presented below.
[b]Isolated yields.

Alkyl halides, particularly alkyl bromides and alkyl chlorides, rapidly reacted with the calcium species of the present invention at temperatures as low as $-78°$ C.

30.3, 29.6, 29.3, 25.9, 22.9, 22.7, 22.3, 14.1; MS (EI) m/e (relative intensity) 212 (M$^+$, 1.2), 194 (5.8), 183 (1.5), 169 (23.5), 141 (11.4), 127 (10.9), 109 (13.6), 99 (100.0), 81 ( 67.0); High Resolution Mass Spec. (HRMS) calcd. for $C_{14}H_{28}O$ m/e 212.2140, found m/e 212.2137.

1-Phenylcyclohexanol (85% yield): mp 62°-63° C.; IR (KBr) 3336, 3059, 3030, 1444, 1381, 1259, 1134, 1032, 974, 756, 696 cm$^{-1}$; $^1$H NMR (360 MHz, CDCl$_3$) δ 7.20–7.55 (m, 5 H), 1.20–1.92 (m, 11 H); $^{13}$C NMR (50 MHz, CDCl$_3$) δ 149.4, 128.2, 126.7, 124.6, 73.1, 38.8, 25.5, 22.2.

1-(m-Methylphenyl)cyclohexanol (76% yield): IR (neat) 3406, 3024, 2931, 2856, 1606, 1446, 1259, 1167, 1132, 1036, 972, 783, 704 cm$^{-1}$; $^1$H NMR (200 MHz, CDCl$_3$) δ 7.02–7.35 (m, 4 H), 2.36 (s, 3 H), 1.57–1.88 (m, 11 H); $^{13}$C NMR (50 MHz, CDCl$_3$) δ 149.4, 137.7, 128.1, 127.4, 125.3, 121.6, 73.1, 38.8, 25.5, 22.2, 21.6. Known compound: $^1$H-NMR, see Sadtler 33855.

1-Cyclohexylcyclohexanol (75% yield): IR (KBr) 3469, 2929, 2850, 1446, 1254, 1165, 1132, 960 cm$^{-1}$; $^1$H NMR (200 MHz, CDCl$_3$) δ 0.80–1.90 (m, 22 H); $^{13}$C NMR (50 MHz, CDCl$_3$) δ 73.0, 48.2, 34.3, 26.9, 26.6, 26.5, 26.0, 21.9.

1-(3-Phenoxypropyl)cyclohexanol (75% yield): IR (neat) 3433, 2931, 2858, 1601, 1587, 1496, 1246, 754, 690 cm$^{-1}$; $^1$H NMR (200 MHz, CDCl$_3$) δ 7.20–7.32 (m, 2 H), 6.84–6.97 (m, 3 H), 3.96 (t, 2 H, J=6.3 Hz), 1.15–1.95 (m, 15 H); $^{13}$C NMR (50 MHz, CDCl$_3$) δ 158.9, 129.3, 120.5, 114.5, 71.0, 68.3, 38.6, 37.4, 25.8, 23.0, 22.2; MS (EI) m/e (relative intensity) 234 (M$^+$, 1.4), 216 (0.7), 191 (1.2), 141 (52.5), 123 (32.1), 120 (34.7), 99 (42.0), 94 (90.9), 81 (100.0); HRMS calcd. for $C_{15}H_{22}O_2$ m/e 234.1620, found m/e 234.1625. Anal. Calcd.: C, 76.88; H, 9.46. Found: C, 76.57; H, 9.55.

1-(m-Methoxyphenyl)cyclohexanol (79% yield): IR (neat) 3437, 2933, 2854, 1601, 1583, 1483, 1448, 1431, 1288, 1265, 1248, 1049, 781, 698 cm$^{-1}$; $^1$H NMR (200 MHz, CDCl$_3$) δ 6.75–7.31 (m, 4 H), 3.81 (s, 3 H), 1.40–1.90 (m, 11 H); $^{13}$C NMR (50 MHz, CDCl$_3$) δ 159.6, 151.3, 129.2, 117.0, 111.8, 110.7, 73.1, 55.2, 38.8, 25.5, 22.2.

1-(1-Adamantyl)cyclohexanol (80% yield): mp 166°-168° C.; IR (KBr) 3465, 2931, 2902, 2844, 1448, 1344, 980, 955, 935 cm$^{-1}$; $^1$H NMR (200 MHz, CDCl$_3$) δ 0.95–2.05 (m, 26 H); $^{13}$C NMR (50 MHz, CDCl$_3$) δ 74.6, 39.1, 37.3, 35.8, 29.8, 28.7, 26.0, 21.9; MS (EI) m/e (relative intensity) 234 (M$^+$, 0.2), 135 (26.0), 98 (100.0); HRMS calcd. for $C_{16}H_{26}O$ m/e 234.1984, found m/e 234.1982. Anal. Calcd.: C, 81.99; H, 11.18. Found: C, 82.13; H, 11.41.

EXAMPLE 3

Typical Ketone Formation Reaction Using Organocalcium Cuprate Reagents

The following experimental procedure is representative of the reactions set forth below in Table II. The organocalcium reagent (2.72 mmol) was prepared from p-chlorotoluene (344 mg, 2.72 mmol) and highly reactive calcium (3.15 mmol) as described above. CuCN 2LiBr in THF (10 mL) was added to the organocalcium reagent via a cannula at −35° C. The CuCN.2LiBr can be prepared from CuCN and approximately two equivalents of LiBr in THF, as outlined in P. Knochel et at., J. Org. Chem., 53, 2390 (1989), which is incorporated herein by reference. The reaction mixture was stirred at −35° C. for 30 minutes. Benzoyl chloride (950 mg, 6.76 mmol) was added to the mixture via a disposable syringe at −35° C. and the resulting mixture was gradually warmed to room temperature. Saturated aqueous NH$_4$Cl solution (20 mL) was then added to the reaction mixture at room temperature for the purpose of neutralizing the reaction mixture. The reaction mixture was then filtered through a small pad of Celite TM filter agent and was washed with Et$_2$O (50 mL). The aqueous layer was extracted with Et$_2$O (2×30 mL). The combined organic phases were washed with H$_2$O (3×15 mL) and dried over anhydrous MgSO$_4$. Removal of solvent and flash-column chromatography on silica gel (100 g, 230–400 mesh, eluted sequentially with 20:1 hexanes/EtOAc, 15:1 hexanes/EtOAc, and 10:1 hexanes/EtOAc) yielded (4-methylphenyl)phenylmethanone (458 mg, 86% yield): IR (neat) 3058, 3027, 2921, 1658, 1606, 1446, 1317, 1278, 1178, 937, 924, 835, 787, 730, 700 cm$^{-1}$; $^1$H NMR (200 MHz, CDCl$_3$) δ 7.24–7.82 (m, 9 H), 2.43 (s, 3 H); $^{13}$C NMR (50 MHz, CDCl$_3$) δ 196.4, 143.2, 137.9, 134.8, 132.1, 130.3, 129.9, 128.9, 128.2, 21.6.

TABLE II

Cross-Coupling Reactions of Organocalcium Cuprate Reagents with Benzoyl Chloride$^a$

| Entry | Halide | Product$^b$ | % Yield$^c$ |
|---|---|---|---|
| 1 | Cl(CH$_2$)$_7$CH$_3$ | PhC(O)(CH$_2$)$_7$CH$_3$ | 84 |
| 2 | Br(CH$_2$)$_5$OPh | PhC(O)(CH$_2$)$_5$OPh | 76 |
| 3 | Br-c-C$_6$H$_{11}$ | PhC(O)-c-C$_6$H$_{11}$ | 82 |
| 4 | 1-Cl-4-CH$_3$C$_6$H$_4$ | 1-PhC(O)-4-CH$_3$C$_6$H$_4$ | 86 |
| 5 | 1-Br-4-OCH$_3$C$_6$H$_4$ | 1-PhC(O)-4-OCH$_3$C$_6$H$_4$ | 71 |

$^a$Active calcium was prepared by the lithium biphenylide reduction of CaBr$_2$ in THF. CuCN 2LiBr was used for reaction with organocalcium reagents.
$^b$Most products were compared with authentic samples. The new substance, 1-phenyl-6-phenoxy-1-hexanone, has satisfactory IR, $^1$H NMR, $^{13}$C NMR, and high-resolution mass spectral data.
$^c$Isolated yields.

A soluble copper(I) complex, CuCN 2LiBr was used for the reactions with organocalcium reagents to form the copper calcium complexes, i.e., the organocalcium cuprate reagents. The CuCN 2LiBr can be prepared from CuCN and LiBr in THF, as outlined in P. Knochel et at., J. Org. Chem., 53, 2390 (1988), which is incorporated herein by reference. Reaction of these organocalcium cuprate reagents with benzoyl chloride proceeded smoothly at −35° C. to yield ketones in excellent yields. As shown in Table II, the primary alkylcalcium cuprates, n-octyl and (5-phenoxypentyl)calcium cuprate, reacted rapidly with benzoyl chloride at −35° C. to give 1-phenyl-1-nonanone and 1-phenyl-6-phenoxy-1-hexanone in 84% and 76% yield, respectively. The secondary alkylcalcium cuprate, cyclohexyl calcium cuprate, reacted smoothly with benzoyl chloride to form cyclohexylphenylmethanone in 82% yield. The tertiary alkylcalcium cuprate is also expected to undergo this transformation. In the aryl cases, 4-methylphenyl and 4-methoxyphenyl cuprate, for example, also reacted with benzoyl chloride to afford (4-methylphenyl)phenylmethanone and (4-methoxyphenyl)phenylmethanone in 86% and 71% yield, respectively.

(4-Methoxyphenyl)phenylmethanone (71% yield): mp 60°-61° C.; $^1$H NMR (200 MHz, CDCl$_3$) δ 7.42–7.87 (m, 7 H), 6.92–7.01 (m, 2 H), 3.89 (s, 3 H); $^{13}$C NMR (50 MHz, CDCl$_3$) δ 195.4, 163.2, 138.3, 132.5, 131.9, 130.2, 129.7, 128.2, 113.5, 55.5.

1-Phenyl-1-nonanone (84% yield): $^1$H NMR (200 MHz, CDCl$_3$) δ 7.90–8.02 (m, 2 H), 7.38–7.62 (m, 3 H), 2.96 (t, J=7.4 Hz, 2 H), 1.14–1.74 (m, 12 H), 0.88 (t, J=6.5 Hz, 3 H); $^{13}$C NMR (50 MHz, CDCl$_3$) δ 200.5, 137.2, 132.7, 128.5, 128.0, 38.6, 31.8, 29.4, 29.4, 29.1, 24.4, 22.6, 14.0.

1-Phenyl-6-phenoxy-1-hexanone (76% yield): mp 53.5°-54.5° C.; IR (KBr) 3059, 2941, 2900, 2869, 1678, 1599, 1498, 1475, 1244, 752, 729, 687 cm$^{-1}$; $^1$H NMR (200 MHz, CDCl$_3$) δ 7.92–8.00 (m, 2 H), 7.19–7.60 (m, 5 H), 6.84–6.98 (m, 3 H), 3.97 (t, J=6.4 Hz, 2 H), 3.00 (t, J=7.3 Hz, 2 H), 1.48–1.93 (m, 6 H); $^{13}$C NMR (50 MHz, CDCl$_3$) δ 200.2, 159.0, 137.0, 132.9, 129.4, 128.5, 128.0, 120.5, 114.4, 67.5, 38.4, 29.2, 25.8, 24.0; MS (EI) m/e (relative intensity) 268 (M+, 3.2), 175 (45.3), 105 (100.0), 94 (20.3), 77 (30.0); HRMS calcd. for C$_{18}$H$_{20}$O$_2$ m/e 268.1463, found m/e 268.1459. Anal. Calcd.: C, 80.56; H, 7.51. Found: C, 80.63; H, 7.69.

Cyclohexylphenylmethanone (82% yield): mp 54°–56° C.; IR (KBr) 2927, 2850, 1668, 1595, 1577, 1444, 1252, 1209, 974, 703 cm$^{-1}$; $^1$H NMR (200 MHz, CDCl$_3$) δ 7.90–8.00 (m, 2 H), 7.38–7.60 (m, 3 H), 3.16–3.35 (m, 1 H), 1.14–1.97 (m, 10 H); $^{13}$C NMR (50 MHz, CDCl$_3$) δ 203.8, 136.3, 132.7, 128.5, 128.2, 45.6, 29.4, 25.9, 25.8. The spectral data are identical to the authentic sample. Commercially available compound from Aldrich Chemical Co., Milwaukee, Wis., has mp=55°–57° C.

EXAMPLE 4

Conjugate 1,4-Addition Reactions Using Organocalcium Cuprate Reagents

The following experimental procedure is representative of the reactions set forth below in Table III. The organocalcium reagent (2.66 mmol) was prepared from 1-chlorooctane (395 mg, 2.66 mmol) and highly reactive calcium (3.10 mmol) as described above. An organocalcium cuprate reagent was prepared by adding lithium 2-thienylcyanocuprate (Aldrich Chemical Co., Milwaukee, Wis., 0.25M in THF, 14 mL, 3.50 mmol) to the calcium reagent via a syringe at −50° C. The reaction mixture was gradually warmed to −35° C. over a 30 minute period. The reaction mixture was cooled to −50° C. and 2-cyclohexen-1-one (210 mg, 2.18 mmol) was added via a disposable syringe. The resulting mixture was gradually warmed to room temperature. Saturated aqueous NH$_4$Cl solution (20 mL) was added at room temperature. The reaction mixture was then filtered through a small pad of Celite TM filter agent and was washed with Et$_2$O (50 mL). The aqueous layer was extracted with Et$_2$O (2×30 mL). The combined organic phases were washed with H$_2$O (3×15 mL) and dried over anhydrous MgSO$_4$. Removal of solvent and flash-column chromatography on silica gel (70 g, 230–400 mesh, eluted sequentially with 50:1 hexanes/EtOAc and 10:1 hexanes/EtOAc) gave 3-octylcyclohexanone (401 mg, 87% yield): IR (neat) 2954, 2925, 2854, 1714, 1458, 1225 cm$^{-1}$; $^1$H NMR (200 MHz, CDCl$_3$) δ 1.10–2.50 (m, 23 H), 0.88 (t, J=6.4 Hz, 3 H); $^{13}$C NMR (50 MHz, CDCl$_3$) δ 212.0, 48.2, 41.5, 39.1, 36.6, 31.8, 31.3, 29.7, 29.5, 29.2, 26.6, 25.3, 22.6, 14.1.

TABLE III

Conjugate 1,4-Addition Reactions of Calcium Organocuprate Reagents with Enones

| Entry | Halide | Cu(I) salt | Enone | Product[a] | % Yield[b] |
|---|---|---|---|---|---|
| 1 | Cl(CH$_2$)$_7$CH$_3$ | CuCN—2LiBr | cyclohex-2-enone | 3-octylcyclohexanone | 46 |
| 2 | Cl(CH$_2$)$_7$CH$_3$ | Li-thienyl-CuCN | cyclohex-2-enone | 3-octylcyclohexanone | 87 |
| 3 | Cl(CH$_2$)$_7$CH$_3$ | Li-thienyl-CuCN | CH$_3$CH$_2$C(O)CH=CHCH$_3$ | EtC(O)CH$_2$CH(CH$_3$)(CH$_2$)$_7$CH$_3$ | 47 |
| 4 | Cl(CH$_2$)$_7$CH$_3$ | Li-thienyl-CuCN | isophorone | 3-octyl-3,5,5-trimethylcyclohexanone | <3 |
| 5 | Cl(CH$_2$)$_7$CH$_3$ | Li-thienyl-CuCN | isophorone | 3-octyl-3,5,5-trimethylcyclohexanone | 84 |

+TMSCl & BF$_3$.Et$_2$

TABLE III-continued

Conjugate 1,4-Addition Reactions of Calcium Organocuprate Reagents with Enones

| Entry | Halide | Cu(I) salt | Enone | Product[a] | % Yield[b] |
|---|---|---|---|---|---|
| 6 | Cl–C6H4–CH3 | Li–(2-thienyl)–CuCN | 2-cyclohexenone | 3-(p-methylphenyl)cyclohexanone (C6H4(p-CH3)) | 68 |

[a] Most products were compared with authentic samples. The new substance, 3-(p-methylphenyl)cyclohexanone, has satisfactory IR, $^1$H NMR, $^{13}$C NMR, and high-resolution mass spectra data.
[b] Isolated yields.

The organocalcium cuprate reagents of the present invention undergo conjugate 1,4-addition reactions with α,β-unsaturated ketones. n-Octyl calcium cuprate, generated by reaction of the n-octanocalcium compound with CuCN 2LiBr, reacted with 2-cyclohexenone to give 3-octylcyclohexanone in moderate yield (46% yield). However, a more reactive calcium cuprate species was produced and the yield was greatly improved to 87% when lithium 2-thienylcyanocuprate (available from Aldrich Chemical Company, Inc., Milwaukee, Wis.) was used. This organocalcium cuprate reagent also underwent the conjugate addition with acyclic enones, e.g., 2-hexen-4-one, to give 5-methyl-3-tridecanone in 47% yield; however, further optimization of the yield is possible. Reaction of this organocalcium cuprate reagent with a sterically hindered enone, for example isophorone, produced less than 3% of the desired compound in 24 hours. The isolated yield, however, increased to 84% when the additives BF$_3$ etherate and chlorotrimethylsilane (TMSCl) were used. In the aryl case, p-tolyl calcium cuprate also underwent this transformation with 2-cyclohexenone to give 3-(p-methylphenyl)cyclohexanone in reasonable yield.

5-Methyl-3-tridecanone (46% yield): IR (neat) 2958, 2927, 2856, 1718, 1460, 1414, 1376 cm$^{-1}$; $^1$H NMR (200 MHz, CDCl$_3$) δ 1.90–2.47 (m, 5 H), 1.10–1.40 (m, 14 H), 1.04 (t, J=7.3 Hz, 3 H), 0.88 (t, J=6.4 Hz, 3 H), 0.88 (d, J=6.6 Hz, 3 H); $^{13}$C NMR (50 MHz, CDCl$_3$) δ 211.6, 49.9, 37.0, 36.4, 31.8, 29.7, 29.6, 29.3, 29.3, 26.9, 22.6, 19.8, 14.0, 7.7.

3-(p-methylphenyl)cyclohexanone (68% yield): IR (neat) 3020, 2935, 2864, 1712, 1516, 1446, 1421, 1313, 1248, 1223, 806 cm$^{-1}$; $^1$H NMR (200 MHz, CDCl$_3$) δ 7.01–7.32 (m, 4 H), 2.88–3.06 (m, 1 H), 2.32 (s, 3 H), 1.66–2.67 (m, 8 H); $^{13}$C NMR (50 MHz, CDCl$_3$) δ 210.9, 141.4, 136.1, 129.3, 126.4, 49.0, 44.3, 41.1, 32.8, 25.5, 20.9; Electron Impact MS (EI) m/e (relative intensity) 188 (M$^+$, 60.8), 173 (4.4), 145 (19.8), 131 (100.0), 118 (31.1), 105 (14.9), 91 (13.5); HRMS calcd. for C$_{13}$H$_{16}$O m/e 188.1201, found m/e 188.1209. Anal. Calcd.: C, 82.94; H, 8.57. Found: C, 82.83; H, 8.60.

3,5,5-Trimethyl-3-octylcyclohexanone (84% yield): IR (neat) 2954, 2927, 2856, 1714, 1466, 1281, 1226 cm$^{-1}$; $^1$H NMR (200 MHz, CDCl$_3$) δ 2.04–2.24 (m, 4 H), 1.63 (d, J=14.2 Hz, 1 H), 1.49 (d, J=14.2 Hz, 1 H), 1.16–1.38 (m, 14 H), 1.05 (s, 3 H), 1.04 (s, 3 H), 0.99 (s, 3 H), 0.88 (t, J=6.5 Hz, 3 H); $^{13}$C NMR (50 MHz, CDCl$_3$) δ 212.5, 54.3, 53.2, 49.0, 44.8, 38.7, 36.0, 32.2, 31.8, 30.7, 30.3, 29.5, 29.3, 27.5, 23.7, 22.6, 14.1. Anal. Calcd. for C$_{17}$H$_{32}$O: C, 80.89; H, 12.78. Found: C, 80.50; H, 12.80.

EXAMPLE 5

Reaction of the Highly Reactive Calcium Species with 1,3-Dienes

The following experimental procedure is representative of the reactions set forth below in Table IV. Highly reactive calcium (5.02 mmol) was prepared from CaI$_2$ (5.02 mmol) and lithium biphenylide (10.30 mmol) in THF (20 mL) as described above. To this highly reactive calcium solution, trans,trans-1,4-diphenyl-1,3-butadiene (0.863 g, 4.18 mmol) in THF (10 mL) was added at room temperature to form an organocalcium reagent. (An internal standard n-dodecane was added with starting material for the GC analyses in the cases of 2,3-dimethyl-1,3-butadiene.) After being stirred at room temperature for 30 minutes, the reaction mixture of the organocalcium reagent was cooled to −78° C. and excess 1,3-dibromopropane (1.020 g, 5.05 mmol) was added via a disposable syringe at −78° C. The reaction was monitored by GC (OV-17 column). (In the cases of 2,3-dimethyl-1,3-butadiene, GC yields were reported based on the analyses of reaction quenches by an OV-17 column.) The reaction mixture was gradually warmed to −60° C. and stirred at −60° C. for 1 hour. Saturated aqueous NH$_4$Cl solution (20 mL) was then added at −40° C. The reaction mixture was filtered through a small pad of Celite TM filter agent and was washed with Et$_2$O (30 mL). The aqueous layer was extracted with Et$_2$O (2×30 mL). The combined organic phases were washed with H$_2$O and brine and dried over anhydrous MgSO$_4$. Removal of solvent and flash-column chromatography on silica gel (200 g, 230–400 mesh, eluted sequentially with hexanes and 1% Et$_2$O/hexanes) afforded trans-(1-phenyl)-2-(trans-β-styrenyl)cyclopentane (940 mg, 91% yield): IR (neat) 3080, 3059, 3024, 2952, 2868, 1599, 1495, 1448, 964, 744, 694 cm$^{-1}$; $^1$H NMR (200 MHz, CDCl$_3$) δ 7.01–7.33 (m, 10 H), 6.06–6.27 (m, 2 H), 2.57–2.88 (m, 2 H), 1.99–2.66 (m, 2 H), 1.55–1.95 (m, 4 H); $^{13}$C NMR (50 MHz, CDCl$_3$) δ 144.5, 137.4, 133.5, 129.2, 128.4, 128.2, 127.5, 126.7, 126.0, 125.9, 52.7, 51.6, 35.0, 33.2, 24.2. Anal. Calcd. for C$_{19}$H$_{20}$: C, 91.88; H, 8.12. Found: C, 91.87; H, 8.22.

TABLE IV

Reactions of 1,3-Diene/Calcium Complex with Organic Dihalides[a]

| Entry | Diene | Li/Ar | CaX₂ | Electrophile | Product[b] | % Yield[c] |
|---|---|---|---|---|---|---|
| 1 | Ph—/=\—Ph | Li/Biph | CaI₂ | Br(CH₂)₃Br | (vinyl-cyclopentane with two Ph groups) | 91 |
| 2 | Ph—/=\—Ph | Li/Np | — | Br(CH₂)₃Br | (vinyl-cyclopentane with two Ph groups) | 51[d] |
| 3 | Ph—/=\—Ph | Li/— | CaI₂ | Br(CH₂)₃Br | (vinyl-cyclopentane with two Ph groups) | 74[e] |
| 4 | Ph—/=\—Ph | Li/Biph | CaI₂ | Br(CH₂)₃Br | (vinyl-cyclopentane with two Ph groups) | 53 |
| 5 | Ph—/=\—Ph | Li/Biph | CaI₂ | Br(CH₂)₃Br | (cyclohexene with two Ph groups) | 7[f] |
| 6 | Ph—/=\—Ph | Li/Biph | CaI₂ | Cl(CH₂)₂Cl | (cyclohexene with two Ph groups) | 80[g] |
| 7 | Ph—/=\—Ph | Li/Biph | CaI₂ | ClCH₂Cl | (vinyl-cyclopropane with two Ph groups) | 47[h] |
| 8 | Ph—/=\—Ph | Li/Biph | CaI₂ | (CH₃)₂SiCl₂ | (silacyclopentene with two Ph and two CH₃ groups) | —[i] |
| 9 | (2,3-dimethylbutadiene) | Li/Biph | CaI₂ | Cl(CH₂)₃Cl | (isopropenyl-cyclopentane) | (98)[j] |
| 10 | (2,3-dimethylbutadiene) | Li/Biph | — | Cl(CH₂)₃Cl | (isopropenyl-cyclopentane) | (25) |
| 11 | (2,3-dimethylbutadiene) | Li/Biph | CaI₂ | Cl(CH₂)₄Cl | (isopropenyl-cyclopentane) | (36)[j] |
| 12 | (2,3-dimethylbutadiene) | Li/Biph | CaI₂ | Br(CH₂)₄Br | (isopropenyl-cyclopentane) | (54)[j] |

TABLE IV-continued
Reactions of 1,3-Diene/Calcium Complex with Organic Dihalides[a]

| Entry | Diene | Li/Ar | CaX$_2$ | Electrophile | Product[b] | % Yield[c] |
|---|---|---|---|---|---|---|
| 13 | (diene structure) | Li/Biph | CaI$_2$ | Ph$_2$SiCl$_2$ | (silacyclopentene structure with Si, Ph, Ph) | (89)[k] |

[a] The active calcium was prepared from 2.05 equivalents of preformed lithium biphenylide and 1.0 equivalent of CaI$_2$.
[b] The known products were compared with the authentic sample. All new substances have satisfactory spectroscopic data including IR, $^1$H NMR, $^{13}$C NMR, and high-resolution mass spectral data.
[c] Isolated yields. GC yields are given in parentheses.
[d] 31% starting material was recovered.
[e] No starting material was recovered.
[f] 72% starting material was recovered.
[g] 8% starting material was recovered.
[h] 43% starting material was recovered.
[i] Isolation was difficult because of overlapping with biphenyl.
[j] Product was isolated by distillation.
[k] Product was isolated by reverse-phase thin-layer chromatography.

The reactivity of the calcium metallocycles was significant with excellent chemical yields. For example, 1,4-diphenyl-1,3-butadiene/calcium complex reacted rapidly with 1,3-dibromopropane and 1,4-dibromobutane to form trans-1-phenyl-2-trans-β-styrenylcyclopentane and trans-1-phenyl-2-trans-β-styrenylcyclohexane in 91% and 53% isolated yield, respectively. The stereochemistry of these reactions was always stereospecific.

Reaction of (1,4-diphenyl-2-butene-1,4-diyl)calcium complexes with α,ω-alkylene dihalides usually gave 1,2-addition products while 1,4-addition was always observed in reactions with dichlorosilane. Treatment of (1,4-diphenyl-2-butene-1,4-diyl)calcium complex with 1,2-dibromoethane yielded 7% of the 1,4-addition product, cis-3,6-diphenylcyclohexene, along with 72% of the starting material. The stereochemistry of 3,6-diphenylcyclohex-1-ene was identified by converting the cyclohexene to 1,2-cyclohexanediol via the epoxide (see Example 6 for details). In sum, treatment of 3,6-diphenylcyclohex-1-ene with m-chloroperbenzoic acid in the presence of K$_2$CO$_3$ in CH$_2$Cl$_2$ gave only a single product in 60% yield along with 20% of recovered starting material. The fully decoupled $^{13}$C-NMR spectrum gave only seven peaks which unambiguously proved that two phenyl groups were in cis geometry. Reaction of the epoxide with 6% HClO$_4$ in acetone yielded 1,4-diphenylcyclohexan-2,3-diol in 93% yield. The proton spin-spin coupling constants further verified that the two phenyl groups were cis (see Example 6).

The yield of the 6-membered ring product was increased to 80% and the amount of recovered starting material dropped to 8% when 1,2-dichloroethane was used (entry 6, Table IV). The higher reduction potential of 1,2-dichloroethane presumably eliminated most of the simple electron transfer pathway. Interestingly, reaction of this calcium complex with dichloromethane afforded only the 1,2-addition product, trans-1-phenyl-2-trans-β-styrenylcyclopropane in 47% yield (entry 7, Table IV) along with 43% of 1,4-diphenyl-1,3-butadiene.

Reduction of 1,4-diphenyl-1,3-butadiene with 2.2 equivalents of preformed lithium naphthalenide without the presence of Ca(II) salt, followed by the addition of 1,3-dibromopropane, also yielded the same cyclopentane derivative, but the yield was substantially lower than that obtained in the presence of calcium salts. Also of note is the fact that in the absence of calcium salts over 30% of the starting material was recovered. A similar result was also noted in the nonactivated diene system. The yield dramatically decreased from 98% to 25% in the similar experiments using 2,3-dimethyl-1,3-butadiene with 1,3-dichloropropane. Thus, the observed chemistry is dramatically different when the calcium salts are present.

Direct reduction of the 1,3-dienes with lithium metal in the absence of electron carriers was also carried out. Reduction of 1,4-diphenyl-1,3-butadiene with 2.5 equivalents of lithium metal in THF, followed by the sequential addition of 2.0 equivalents of CaI$_2$ and 1,3-dibromopropane, yielded the same 5-membered ring product in 74% yield along with a small amount of unidentified high molecular weight material. Significantly, no starting material was found in the reaction workup. This shows that the involvement of calcium ions is significant.

This chemistry can also be extended to 2,3-dimethyl-1,3-butadiene, which is a molecule which is much more difficult to reduce. The calcium complex was readily prepared by reacting freshly distilled 2,3-dimethyl-1,3-butadiene with either the biphenylide complex or the calcium naphthalenide complex. Reaction of the resulting complex with 1,3-dichloropropane and 1,4-dichlorobutane gave the 5-membered ring product and 6-membered ring product in 94% and 36% yield, respectively. For the latter reaction, the yield was improved to 54% when 1,4-dibromobutane was used. Similarly, treatment of (2,3-dimethyl-2-butene-1,4-diyl)-calcium complex with dichlorodiphenylsilane yielded the 1,4-addition adduct in 89% yield.

trans-(1-Phenyl)-2-(trans-β-styrenyl)cyclohexane (53% yield): IR (neat) 3082, 3059, 3026, 2924, 2850, 1601, 1495, 1446, 962, 744, 698 cm$^{-1}$; $^1$H NMR (200 MHz, CDCl$_3$) δ 7.02–7.30 (m, 10 H), 6.11 (d, J=15.9 Hz, 1 H), 5.82–5.98 (m, 1 H), 2.28–2.47 (m, 2 H), 1.25–2.02 (m, 8 H); $^{13}$C NMR (50 MHz, CDCl$_3$) δ 146.0, 138.0, 135.0, 128.8, 128.3, 128.2, 127.6, 126.6, 125.9 (2C), 50.6, 46.4, 35.4, 33.3, 26.7, 26.1. Anal. Calcd. for C$_{20}$H$_{22}$: C, 91.55; H, 8.45. Found: C, 91.37; H, 8.10.

cis-3,6-Diphenyl-1-cyclohexene (80% yield): IR (neat) 3080, 3059, 3024, 2931, 2856, 1601, 1493, 1450, 754, 698 cm$^{-1}$; $^1$H NMR (200 MHz, CDCl$_3$) δ 7.16–7.36 (m, 10 H), 5.98 (d, J=1.3 Hz, 2 H), 3.45–3.55 (m, 2 H), 1.87–2.07 (m, 2 H), 1.60–1.79 (m, 2 H); $^{13}$C NMR (50 MHz, CDCl$_3$) δ 145.9, 131.1, 128.3, 127.9, 126.1, 41.2, 29.3 cm$^{-1}$; MS (EI) m/e (relative intensity) 234 (M$^+$, 15.4), 206 (2.7), 143 (10.8), 130 (100.0), 115

(25.3), 104 (24.8), 91 (21.1), 77 (6.3); HRMS calcd. for $C_{18}H_{18}$ m/e 234.1409, found m/e 234.1409.

trans-(1-Phenyl)-2-(trans-$\beta$-styrenyl)cyclopropane (47% yield): IR (neat) 3080, 3059, 3024, 2966, 2929, 1647, 1605, 1496, 1460, 1448, 958, 750, 739, 694 cm$^{-1}$; $^1$H NMR (200 MHz, CDCl$_3$) $\delta$ 7.04–7.35 (m, 10 H), 6.47 (d, J=15.8 Hz, 1 H), 5.90 (dd, J=15.8, 8.6 Hz, 1 H), 2.03 (ddd, J=8.8, 5.5, 4.3 Hz, 1 H), 1.82 (ddt, J=8.6, 5.6, 4.3 Hz, 1 H), 1.31 (dt, J=8.5, 5.4 Hz, 1 H), 1.21 (dt, J=8.8, 5.4 Hz, 1 H); $^{13}$C NMR (50 MHz, CDCl$_3$) $\delta$ 142.1, 137.5, 132.8, 128.5 (2C), 128.4, 128.2, 126.8, 125.7 (2C), 27.4, 25.7, 17.1 cm$^{-1}$; MS (EI) m/e (relative intensity) 220 (M+, 30.6), 142 (8.0), 129 (100.0), 115 (25.1), 103 (3.6), 91 (28.8), 77 (9.5); HRMS calcd. for $C_{17}H_{16}$ m/e 220.1252, found m/e 220.1252.

cis-1,1-Dimethyl-2,5-diphenylsilacyclopent-3-ene: IR (neat) 3078, 3059, 3020, 2954, 2895, 2850, 1599, 1495, 1250, 1061, 858, 802, 746, 698 cm$^{-1}$; $^1$H NMR (200 MHz, CDCl$_3$) $\delta$ 7.00–7.30 (m, 10 H), 6.11 (s, 2 H), 3.27 (s, 2 H), 0.39 (s, 3 H), −0.67 (s, 3 H); $^{13}$C NMR (50 MHz, CDCl$_3$) $\delta$ 143.4, 135.0, 128.3, 126.4, 124.3, 39.9, −2.8, −6.8.

1,1-Diphenyl-3,4-dimethylsilacyclopent-3-ene (89% GC yield): IR (neat) 3066, 3049, 2976, 2906, 2871, 1427, 1174, 1117, 773, 731, 698 cm$^{-1}$; $^1$H NMR (200 MHz, CDCl$_3$) $\delta$ 7.27–7.62 (m, 10 H), 1.87 (s, 2 H), 1.77 (s, 3 H); $^{13}$C NMR (50 MHz, CDCl$_3$) $\delta$ 136.4, 134.7, 130.7, 129.3, 127.8, 24.2, 19.3.

1-Methyl-1-(2-propenyl)cyclopentane (94% GC yield): IR (neat) 2958, 2871, 1639, 1452, 1369, 889 cm$^{-1}$; $^1$H NMR (200 MHz, CDCl$_3$) $\delta$ 4.65–4.73 (m, 2H), 1.76 (dd, J=1.3, 0.7 Hz, 3H), 1.35–1.73 (m, 8H), 1.05 (s, 3H); $^{13}$C NMR (50 MHz, CDCl$_3$) $\delta$ 153.3, 107.6, 48.0, 37.7, 26.0, 23.7, 20.2.

1-Methyl-1-(2-propenyl)cyclohexane (54% GC yield): $^1$H NMR (200 MHz, CDCl$_3$) $\delta$ 4.72–4.82 (m, 2H), 1.71 (dd, J=1.4, 0.7 Hz, 3H), 1.20–1.75 (m, 10H), 0.98 (s, 3H); $^{13}$C NMR (50 MHz, CDCl$_3$) $\delta$ 152.6, 109.1, 38.8, 36.4, 27.1, 26.4, 22.6, 19.5.

EXAMPLE 6

Synthesis of 1,2-Epoxy-3,6-diphenylcyclohexane and 3,6-Diphenylcyclohexan-1,2-diol 1,2-Epoxy-3,6-diphenylcyclohexane: 3,6-Diphenylcyclohex-1-ene (50 mg, 0.21 mmol), m-chloroperbenzoic acid (55%, 200 mg, 0.64 mmol), and K$_2$CO$_3$ (150 mg, 1.09 mmol) were stirred in CH$_2$Cl$_2$ (10 mL) for 24 hours. The reaction mixture was filtered and washed with CH$_2$Cl$_2$ (40 mL). The filtrate and aqueous Na$_2$S$_2$O$_3$ solution (10%, 10 mL) were stirred for 2 hours. The organic phase was washed with saturated NaHCO$_3$ solution and H$_2$O and dried over anhydrous magnesium sulfate. Preparative thin-layer chromatography (silica gel, 2 mm, developed with 10:1 hexane/EtOAc) gave 1,2-epoxy-3,6-diphenylcyclohexane (32 mg, 60% yield) as a colorless oil along with recovery of starting material (10 mg, 20%). 1,2-Epoxy-3,6-diphenylcyclohexane: $^1$H NMR (200 MHz, CDCl$_3$) $\delta$ 7.20–7.45 (m, 10 H), 3.45 (s, 2 H), 3.37 (t, J=6.4 Hz, 2 H), 1.67–1.88 (m, 2 H), 1.37–1.58 (m, 2 H); $^{13}$C NMR (50 MHz), 143.2, 128.6, 128.0, 126.5, 56.2, 39.9, 25.0.

3,6-Diphenylcyclohexan-1,2-diol: 1,2-Epoxy-3,6-diphenylcyclohexane (32 mg, 0.13 mmol) was dissolved in acetone (10 mL). HClO$_4$ (6%, 10 mL) was added and the mixture was stirred at room temperature for 24 hours. The reaction solution was neutralized with Na$_2$CO$_3$ and the reaction mixture was reduced to approximately half volume under reduced pressure. Extraction with CH$_2$Cl$_2$ and removal of the solvent yielded crude product (93% yield) as a white solid. Based upon the analyses of NMR spectra of crude and recrystallized product, reaction gave a single product. Recrystallization from hexane/CH$_2$Cl$_2$ gave pure product as a white crystalline solid: mp 134°–135° C.; IR (KBr) 3303, 3086, 3059, 3026, 2935, 2858, 1603, 1495, 1454, 1041, 760, 698 cm$^{-1}$; $^1$H NMR (200 MHz, CDCl$_3$) $\delta$ 7.20–7.60 (m, 10 H), 4.08 (t, J=9.8 Hz, 1 H), 3.95 (dd, J=9.5, 5.5 Hz, 1 H), 3.56 (m, 1 H), 2.67 (ddd, J=11.7, 9.9, 4.3 Hz, 1 H), 1.65–2.39 (m, 6 H); $^{13}$C NMR (50 MHz, CDCl$_3$) $\delta$ 142.3, 140.8, 129.7, 128.8, 128.4, 127.8, 126.9, 126.5, 76.8, 74.6, 50.6, 44.7, 29.9, 29.2; MS (EI) m/e (relative intensity) 268 (M+, 61.9), 250 (12.9), 237 (11.5), 219 (7.3), 146 (30.1), 131 (94.9), 117 (55.4), 104 (100.0), 91 (73.6), 77 (15.3); HRMS calcd. for $C_{18}H_{20}O_2$ m/e 268.1463, found m/e 268.1464.

EXAMPLE 7

Preparation of Polymeric Compounds From Organocalcium Dihalides

Poly(paraphenylene ketone): Highly reactive calcium (4.00 mmol), prepared from lithium biphenylide (8.36 mmol) and CaI$_2$ (4.00 mmol) in THF (30 mL), was cooled to −78° C. This solution was added dropwise via cannula into a solution of 1,4-dibromobenzene (2.01 mmol) at −78° C. over a period of 1 hour. The reaction mixture was added to terephthaloyl chloride (2.01 mmol) in THF (10 mL) at −78° C. and stirred for 30 minutes. It was allowed to warm to room temperature and then refluxed for 30 minutes. The reaction mixture was then cooled to room temperature and 10% HCl (10 mL) was added with stirring. The mixture was stirred for an additional 30 minutes, and then added to methanol (200 mL). The solid was filtered and washed several times with 200 mL portions of methanol and 10% HCl. The solid was dried under vacuum at 100° C. for 24 hours. A brown powder (0.3865 g, 93% yield) of —(—C$_6$H$_4$C(O)—)$_n$— resulted. FTIR (diffuse reflectance): observed an intense peak at 1665 cm$^{-1}$ for carbonyl (C=O).

Poly(paraphenylene): Highly reactive calcium (4.61 mmol), prepared from lithium biphenylide (9.36 mmol) and CaI$_2$ (4.61 mmol) in THF (30 mL), was cooled to −78° C. This solution was added dropwise via cannula into a solution of 1,4-dibromobenzene (4.62 mmol) at −78° C. over a period of 20 minutes. The solution was stirred for an additional 80 minutes at −78° C., and then it was allowed to warm to room temperature over the course of 20 minutes. A solution of NiCl$_2$ (0.077 mmol) in THF (5 mL) was added to the reaction mixture, and then refluxed for 4 hours. The solution became dark gray in color, 10% HCl (10 mL) was added, and then this was added to methanol (300 mL). A solid was filtered from the reaction mixture and washed with 500 mL portions of methanol and 10% HCl. The solid was dried under vacuum at 80° C. for 30 hours. A light yellow powder (0.1622 g, 42% yield) of —(—C$_6$H$_4$—)$_n$— resulted. FTIR (diffuse reflectance): observed peaks at 808 cm$^{-1}$ for para-substituted benzene, 1075 cm$^{-1}$ for aryl C-Br, and at 692 and 764 cm$^{-1}$ for aryl C-H. Elemental Analysis: Found: C=87.44, H=5.30, Br=3.70. Calcd. for n=13 chain length, C=87.55, H=4.96, Br=7.48.

Poly(2,5-thienylene): Highly reactive calcium (3.98 mmol), prepared from lithium biphenylide (8.17 mmol) and CaI$_2$ (3.98 mmol) in THF (15 mL), was cooled to −78° C. This solution was added dropwise via cannula into a solution of 2,5-dibromothiophene (4.04 mmol) at −78° C. over a period of 30 minutes. Upon the addition of the 2,5-dibromothiophene, the color changed from a dark color to a gray color. The solution was allowed to warm to room temperature over the course of 30 minutes. A solution of $NiCl_2$ (0.015 mmol) in THF (10 mL) was added to the reaction mixture, and then refluxed for 15 hours. The solution became dark brown in color 10 minutes after the addition of the $NiCl_2$. The solution was allowed to cool to room temperature and was added to a mixture of 10% HCl (200 mL) and methanol (200 mL). This produced a dark brown precipitate. A solid was filtered from the reaction mixture and washed with 200 mL portions of methanol and 10% HCl. The solid was dried under vacuum at 80° C. for 20 hours. A dark brown powder (0.1182 g, 36% yield) resulted. The product is soluble in THF and acetone, and insoluble in methanol and 10% HCl. FTIR (diffuse reflectance): observed an intense peak at 790 $cm^{-1}$ for C-H out-of-plane vibration for disubstituted thiophene. The peak for C-Br at 980 $cm^{-1}$ was absent.

EXAMPLE 8

Spiroannelation

In a typical preparation, 1,2-dimethylenecyclohexane (2.0 mmol) is added via a disposable syringe to the newly prepared highly reactive Ca (3.0–4.0 mmol) in THF (15 mL). The mixture is stirred for several hours at room temperature under argon. Bis-electrophiles are added to the freshly prepared THF solutions of the calcium complexes of 1,2-dimethylenecycloalkanes at −78° C. The reaction mixture is then stirred at −78° C. prior to warm up to room temperature. This same method can be extended to other 1,2-dimethylenecycloalkanes, such as 1,2-dimethylenecyclopentane and 1,2-dimethylenecycloheptane.

Significantly, treatment of this type of 2-butene-1,4-diylcalcium complex, i.e., those resulting from the reaction of highly reactive calcium with cycloalkanes having two conjugated exocyclic double bonds, with bis-electrophiles, especially 1,n-dibromoalkanes, give spirocycles. Representative examples are summarized in Table V. A major advantage of using 2-butene-1,4-diylcalcium complexes is that spiroannelation can be achieved in one synthetic operation.

TABLE V

| | Reactions of the Calcium Complexes of 1,2-Dimethylenecycloalkanes with Bis-electrophiles | | |
|---|---|---|---|
| Diene[a] | Electrophile | Conditions | Product |
| 1 | $Br(CH_2)_5Br$ | −78° C. to reflux | |
| 1 | $Br(CH_2)_4Br$ | −78° C. to reflux | |
| 1 | $Br(CH_2)_3Br$ | −78° C. to room temp. | |
| 1 | $Br(CH_2)_3Br$ | −78° C. to −30° C. | |
| 1 | $Br(CH_2)_2Br$ | −78° C. to room temp. | |
| 1 | $TsO(CH_2)_2OTs$ | −78° C. to room temp. | |
| 2 | $Br(CH_2)_3Br$ | −78° C. to room temp. | |

TABLE V-continued

Reactions of the Calcium Complexes of
1,2-Dimethylenecycloalkanes with Bis-electrophiles

| Diene[a] | Electrophile | Conditions | Product |
|---|---|---|---|
| 3 | Br(CH$_2$)$_3$Br | −78° C. to room temp. | (structure) |

[a]1: 1,2-Dimethylenecyclohexane; 2: 1,2-Dimethylenecyclopentane; 3: 1,2-Dimethylenecycloheptane.

EXAMPLE 9

Preparation of γ-Lactones Including Spiro γ-Lactones

The 2-butene-1,4-diylcalcium complexes prepared from the reaction of highly reactive calcium with either cyclic hydrocarbons having at least two conjugated exocyclic double bonds or open-chain conjugated dienes, react with a ketone or aldehyde and carbon dioxide to form γ-lactones, preferably spiro γ-lactones. Calcium complexes of 1,2-dimethylenecycloalkanes and 1,3-butadienes are prepared as described above. A molar equivalent of a ketone is added to the THF solution of these complexes at a temperature of about −78° C. The reaction mixture is then stirred, warmed to a temperature of 0° C. to 25° C., and bubbled with carbon dioxide prior to acidic hydrolysis and warming to about 40° C.

In a typical reaction 1,2-dimethylenecyclohexane (0.239 g, 2.21 mmol) is added via a disposable syringe to the highly reactive calcium (3.53 mmol) in THF (20 mL). After being stirred at room temperature for several hours, the reaction mixture is allowed to stand until the solution becomes transparent. The THF solution of newly formed calcium complex of 1,2-dimethylenecyclohexane is cooled to −78° C. using a dry ice/acetone bath, and acetone (0.122 g, 2.10 mmol) is added via a disposable syringe. The mixture is stirred at −78° C., then gradually warmed to 0° C. Carbon dioxide is then bubbled through the reaction mixture at 0° C., and then at room temperature. An aqueous solution of 1.5N HCl (10 mL) is added at 0° C. The reaction mixture is heated slightly to 40° C. After cooling to room temperature, the mixture is extracted with diethyl ether (3×20 mL). The combined organic phases are washed with saturated aqueous NaHCO$_3$ (2×20 mL) and brine (20 mL) and dried over anhydrous MgSO$_4$. Removal of solvents and flash column chromatography gives 4,4-dimethyl-6-methylene-3-oxaspiro[4.5]decan-2-one. See Table VI for representative examples of compounds that can be made by this method.

TABLE VI

Synthesis of Spiro γ-Lactones from
Conjugated Diene, Ketone and CO$_2$

| Entry | Diene[a] | Ketone | Product |
|---|---|---|---|
| 1 | 1 | Acetone | (structure) |
| 2 | 1 | Cyclopentanone | (structure) |
| 3 | 1 | Cyclohexanone | (structure) |
| 4 | 4 | Cyclopentanone | (structure) |
| 5 | 4 | Cyclohexanone | (structure) |

[a]1: 1,2-Dimethylenecyclohexane; 4: 2,3-Dimethyl-1,3-butadiene.

EXAMPLE 10

Preparation of δ-Lactones

In a typical procedure, 1,2-bis(methylene)cyclohexane (0.330 g, 3.05 mmol) is added via a disposable syringe to the active calcium (4.68 mmol) in freshly distilled THF (15 mL). After being stirred at ambient temperature for several hours, the reaction mixture is allowed to stand until the solution becomes transparent. The THF solution of newly formed calcium complex of 1,2-dimethylenecyclohexane is cooled to −78° C. using a dry ice/acetone bath. Ethylene oxide (1 mL) is condensed into a small vial capped with a rubber septum (at −78° C.) and is subsequently added to the reaction mixture via cannula. The mixture is stirred at −78° C. and gradually warmed to 0° C. At this point, the reaction mixture is bubbled with purified carbon dioxide for 10 minutes at 0° C., and continued at room temperature. An aqueous solution of 3N HCl (10 mL) is added via a syringe at 0° C. The reaction mixture is then warmed to 40° C. After subsequent cooling to room temperature, the mixture is extracted with diethyl ether (3×20 mL). The combined organic layers are washed with saturated aqueous NaHCO$_3$ (2×20 mL), water (1×20 mL), and then dried over anhydrous MgSO$_4$. The solvents can be removed under vacuum followed by flash chromatography to afford the δ-lactone product. See Table VII for examples of compounds that can be prepared using this method. If carbon dioxide is not used, and the epoxide/diene-calcium addition adducts are hydrolyzed with acid, alcohols are produced. See Table VIII for examples of compounds that can be prepared using this method.

TABLE VII

Reactions of Conjugated Diene-Calcium Complexes with Epoxides Followed by Carbon Dioxide

| Entry | Diene | Epoxide | Product |
|---|---|---|---|
| 1 | | | |
| 2 | | | |
| 3 | | | |
| 4 | | | |
| 5 | | | |

TABLE VIII

Reactions of Conjugated Diene-Calcium Complexes with Epoxides Followed by Acidic Hydrolysis

| Entry | Diene | Epoxide | Product |
|---|---|---|---|
| 1 | | | |
| 2 | | | |

TABLE VIII-continued

Reactions of Conjugated Diene-Calcium Complexes with Epoxides Followed by Acidic Hydrolysis

| Entry | Diene | Epoxide | Product |
|---|---|---|---|
| 3 | | | |
| 4 | | | |

EXAMPLE 11

Preparation of γ-Lactams

In a typical experiment, 2,3-dimethyl-1,3-butadiene (1.5 mL) is added neat via a disposable syringe to the active calcium (4.64 mmol) in freshly distilled THF (15 mL). After being stirred at ambient temperature for 8 hours, the reaction mixture is allowed to stand until the solution becomes transparent. The THF solution of newly formed calcium-diene complex is then cooled to −78° C. using a dry ice/acetone bath. N-benzylideneaniline (0.547 g, 3.02 mmol) is weighed into a small vial and capped with a rubber septum, evacuated and charged with argon. 5 mL of freshly distilled THF is then added to the vial and this is added via cannula to the calcium-diene solution at −78° C. The reaction mixture is then allowed to warm to 0° C. and is charged with purified carbon dioxide at 0° C., and then continued at room temperature. An aqueous solution of 3N HCl (10 mL) is added to the reaction mixture via a syringe at 0° C. The reaction mixture is then warmed to 40° C. After cooling to room temperature, the mixture is extracted with diethyl ether (3×20 ml). The combined organic layers are washed with saturated aqueous NaHCO$_3$ (2×20 mL), water (1×20 mL), and then dried over anhydrous MgSO$_4$. After removal of solvents under vacuo, the residue is flash chromatographed on silica gel using gradient mixtures of hexanes and ethyl acetate to afford the N-benzyl-γ-lactam.

EXAMPLE 12

Preparation of Chiral Vicinal Diols

In a typical preparation, 1,2-bis(methylene)cyclohexane (0.303 g, 2.80 mmol) is added via a disposable syringe to the active calcium (4.05 mmol) in freshly distilled THF (15 mL). After being stirred at ambient temperature, the reaction mixture is allowed to stand until the solution becomes transparent. The THF solution of newly formed calcium complex of 1,2-dimethylenecyclohexane is cooled to −78° C. using a dry ice/acetone bath. (R)-2-Methylglycidol (0.109 g, 1.24 mmol) is added to the reaction mixture via a disposable syringe at −78° C. and stirred. The reaction mixture is then allowed to slowly warm to 0° C. followed by subsequent addition of NH$_4$Cl (5 mL) via syringe. After warming to room temperature, the reaction mixture is extracted with diethyl ether (3×20 mL) and the combined organic layers are dried over anhydrous MgSO$_4$. After removal of solvents under vacuo, the residue is flash chromatographed on silica gel using gradient mixtures of hexanes and ethyl acetate to afford the vicinal diol as a 1:1 mixture of diastereomers.

The foregoing detailed description has been given for clarity of understanding only and no unnecessary limitations are to be understood therefrom. The invention is not limited to the exact details shown and described, for obvious modifications will occur to those skilled in the art.

What is claimed is:

1. A calcium complex comprising the reaction product of a conjugated diene and a soluble calcium species; said soluble calcium species comprising formally zerovalent calcium metal atoms and a polyene solubilizing agent in an ethereal, polyethereal, or hydrocarbon solvent.

2. The calcium complex of claim 1 wherein the conjugated diene is a cyclic hydrocarbon containing at least two conjugated double bonds.

3. The calcium complex of claim 1 wherein the conjugated diene is an open-chain conjugated diene.

4. A method for the preparation of γ-lactones comprising:
   (a) contacting a calcium(II) salt in an ethereal, polyethereal, or hydrocarbon solvent with reducing agent having a reduction potential of about −1.5 volts, or more negative, relative to SCE, to form a highly reactive calcium species;
   (b) contacting the highly reactive calcium species with a conjugated diene, to form a 2-butene-1,4-diylcalcium complex;
   (c) contacting the 2-butene-1,4-diylcalcium complex with a ketone or aldehyde to form a 1,2-addition adduct of the 2-butene-1,4-diylcalcium complex;
   (d) contacting the 1,2-addition adduct of the 2-butene-1,4-diylcalcium complex with CO$_2$ to form a nucleophilic addition product; and
   (e) contacting the nucleophilic addition product with an aqueous acid to form a γ-lactone.

5. The method of claim 4 wherein the conjugated diene is a cyclic hydrocarbon containing at least two conjugated exocyclic double bonds.

6. The method of claim 4 wherein the conjugated diene is an open-chain conjugated diene.

7. The method of claim 4 wherein the step of contacting the 1,2-addition adduct of the 2-butene-1,4-diylcalcium complex with CO$_2$ is carried out at a temperature of about 0° C. to about 25° C.

8. The method of claim 4 wherein the step of contacting the nucleophilic addition product with an aqueous acid includes a step of warming the reaction mixture to a temperature of about 30° C. to about 50° C.

9. A method for the preparation of δ-lactones comprising:
   (a) contacting a calcium(II) salt in an ethereal, polyethereal, or hydrocarbon solvent with reducing agent having a reduction potential of about −1.5 volts, or more negative, relative to SCE, to form a highly reactive calcium species;

(b) contacting the highly reactive calcium species with a conjugated diene, to form a 2-butene-1,4-diylcalcium complex;

(c) contacting the 2-butene-1,4-diylcalcium complex with an epoxide to form an addition adduct of the 2-butene-1,4-diylcalcium complex and epoxide;

(d) contacting the addition adduct of the 2-butene-1,4-diylcalcium complex and epoxide with $CO_2$ to form a nucleophilic addition product; and (e) contacting the nucleophilic addition product with an aqueous acid to form a δ-lactone.

10. The method of claim 9 wherein the conjugated diene is a cyclic hydrocarbon containing at least two conjugated exocyclic double bonds.

11. The method of claim 9 wherein the conjugated diene is an open-chain conjugated diene.

12. The method of claim 9 wherein the step of contacting the (2-butene-1,4-diyl)calcium complex with an epoxide is carried out at a temperature of about −90° C. to about −70° C.

13. The method of claim 9 wherein the step of contacting the nucleophilic addition product with an aqueous acid includes a step of warming the reaction mixture to a temperature of about 30° C. to about 50° C.

14. The method of claim 9 wherein the epoxide is an unsymmetric epoxide.

15. A method for the preparation of spirocycles comprising:
(a) contacting a calcium(II) salt in an ethereal, polyethereal, or hydrocarbon solvent with a reducing agent having a reduction potential of about −1.5 volts, or more negative relative to SCE, to form a highly reactive calcium species;
(b) contacting the highly reactive calcium species with a cyclic hydrocarbon containing at least two conjugated exocyclic double bonds to form a 2-butene-1,4-diylcalcium complex; and
(c) contacting the 2-butene-1,4-diylcalcium complex with an electrophile to form a spirocycle.

16. The method of claim 15 wherein the electrophiles are selected from the group consisting of organodihalides, organoditosylates, haloalkylnitriles, organoditriflates, esters, and amides.

17. The method of claim 15 wherein the step of contacting the 2-butene-1,4-diylcalcium complex with an electrophile is carried out at a temperature below about 100° C.

18. The method of claim 15 wherein the step of contacting the 2-butene-1,4-diylcalcium complex with an electrophile is carried out in an ethereal or polyethereal solvent.

19. A method for the preparation of γ-lactams comprising:
(a) contacting a calcium(II) salt in an ethereal, polyethereal, or hydrocarbon solvent with reducing agent having a reduction potential of about −1.5 volts, or more negative, relative to SCE, to form a highly reactive calcium species;
(b) contacting the highly reactive calcium species with a conjugated diene, to form a 2-butene-1,4-diylcalcium complex;
(c) contacting the 2-butene-1,4-diylcalcium complex with an imine to form an 1,2-addition adduct of the 2-butene-1,4-diylcalcium complex and imine;
(d) contacting the 1,2-addition adduct of the 2-butene-1,4-diylcalcium complex and imine with $CO_2$ to form a nucleophilic addition product; and (e) contacting the nucleophilic addition product with an aqueous acid to form a γ-lactam.

20. A method for the preparation of chiral vicinal diol comprising:
(a) contacting a calcium(II) salt in an ethereal, polyethereal, or hydrocarbon solvent with reducing agent having a reduction potential of about −1.5 volts, or more negative, relative to SCE, to form a highly reactive calcium species;
(b) contacting the highly reactive calcium species with a conjugated diene, to form a 2-butene-1,4-diylcalcium complex;
(c) contacting the 2-butene-1,4-diylcalcium complex with an unsymmetrical chiral epoxide containing a hydroxyl functional group to form an adduct of the 2-butene-1,4-diylcalcium complex;
(d) contacting the adduct of the 2-butene-1,4-diylcalcium complex with an aqueous acid to form a chiral vicinal diol.

21. A method of preparing an organic polymer comprising:
(a) contacting a calcium salt in an ethereal, polyethereal, or hydrocarbon solvent with a reducing agent having a reduction potential of about −1.5 volts, or more negative relative to SCE, to form a highly reactive calcium species; and
(b) contacting the highly reactive calcium species with a haloarene to form an organic polymer.

22. The method of claim 21 wherein the step of contacting the calcium species with a haloarene includes a step of adding a catalyst.

23. The method of claim 22 wherein the catalyst is $NiCl_2$.

24. The method of claim 22 wherein the haloarene is dihaloarene.

25. The method of claim 24 wherein the dihaloarene is a dihalobenzene.

26. The method of claim 25 wherein the dihalobenzene is 1,4-dibromobenzene and the polymer formed is poly(paraphenylene).

27. The method of claim 24 wherein the dihaloarene is a dihalothiophene.

28. The method of claim 27 wherein the dihalobenzene is 2,5-dibromothiophene and the polymer formed is poly(2,5-thienylene).

29. The method of claim 22 wherein the haloarene is trihaloarene.

30. The method of claim 21 wherein the step of contacting the calcium species with a haloarene includes a step of adding an electrophile.

31. The method of claim 30 wherein the electrophile is terephthaloyl chloride.

32. The method of claim 31 wherein the haloarene is 1,4-dibromobenzene and the polymer formed is poly(paraphenylene ketone).

33. A method of preparing a calcium-substituted fullerene comprising:
(a) contacting a calcium salt in an ethereal, polyethereal, or hydrocarbon solvent with a reducing agent having a reduction potential of about −1.5 volts, or more negative relative to SCE, to form a highly reactive calcium species; and
(b) contacting the highly reactive calcium species with a fullerene to form a calcium-substituted fullerene.

34. The method of claim 33 wherein the calcium-substituted fullerene is mono-substituted.

35. The method of claim 33 wherein the calcium-substituted fullerene is disubstituted.

* * * * *

UNITED STATES PATENT AND TRADEMARK OFFICE
CERTIFICATE OF CORRECTION

PATENT NO. : 5,384,078                       Page 1 of 2
DATED      : January 24, 1995
INVENTOR(S) : Reuben D. Rieke It is certified that error appears in the above-indentified patent and that said Letters Patent is hereby corrected as shown below:

Column 23, lines 11-15, please replace the existing formula with the following formula:

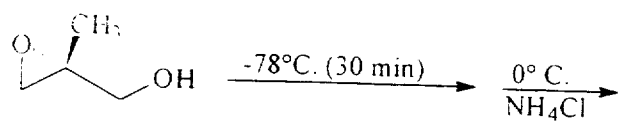

UNITED STATES PATENT AND TRADEMARK OFFICE
CERTIFICATE OF CORRECTION

PATENT NO. : 5,384,078
DATED : Jan. 24, 1995
INVENTOR(S) : Reuben D. Rieke

Page 2 of 2

It is certified that error appears in the above-indentified patent and that said Letters Patent is hereby corrected as shown below:

Columns 15-16, lines 27-54, please replace the existing formula with the following formula:

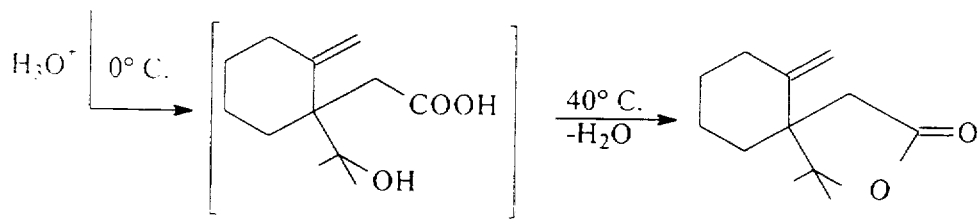

Signed and Sealed this

Thirteenth Day of August, 1996

Attest:

BRUCE LEHMAN

Attesting Officer

Commissioner of Patents and Trademarks